US007686775B2

(12) United States Patent
Branch

(10) Patent No.: US 7,686,775 B2

(45) Date of Patent: Mar. 30, 2010

(54) METHOD AND APPARATUS FOR MULTIDIRECTIONAL POSITIONING OF A SHOULDER

(76) Inventor: Thomas P. Branch, 930 Lullwater Rd., Atlanta, GA (US) 30307

( * ) Notice: Subject to any disclaimer, the term of this patent is extended or adjusted under 35 U.S.C. 154(b) by 395 days.

(21) Appl. No.: 11/104,051

(22) Filed: Apr. 11, 2005

(65) Prior Publication Data

US 2005/0251076 A1 Nov. 10, 2005

Related U.S. Application Data

(60) Provisional application No. 60/561,087, filed on Apr. 9, 2004.

(51) Int. Cl.
*A61F 5/00* (2006.01)

(52) U.S. Cl. .......................................... 602/13; 602/20

(58) Field of Classification Search ..................... 602/5, 602/13, 20–23; 128/877–879

See application file for complete search history.

(56) References Cited

U.S. PATENT DOCUMENTS

| | | | |
|---|---|---|---|
| 1,950,331 | A | 3/1934 | Tornsjo |
| 2,236,411 | A | 3/1941 | Backman |
| 2,427,053 | A | 9/1947 | Hampton |
| 2,543,248 | A | 2/1951 | Gleason |
| 3,581,740 | A | 6/1971 | Sherbourne |
| 3,780,728 | A | 12/1973 | Stader |
| 3,892,230 | A | 7/1975 | Baker et al. |
| 3,906,942 | A | 9/1975 | Lumb, Jr. et al. |
| 3,937,215 | A | 2/1976 | Barthlome |
| 4,146,021 | A | 3/1979 | Brosseau et al. |
| 4,291,715 | A | 9/1981 | Monte |

(Continued)

FOREIGN PATENT DOCUMENTS

| | | |
|---|---|---|
| DE | 92 17 225.3 | 5/1993 |
| WO | WO 99/03440 A1 | 1/1999 |

*Primary Examiner*—Michael A. Brown
(74) *Attorney, Agent, or Firm*—Alston & Bird LLP

(57) ABSTRACT

The invention relates to a method and apparatus for manipulating a shoulder joint, by independently manipulating the upper arm in two directions. One direction is "longitudinal", wherein the upper arm moves substantially along its longitudinal axis. The second is "lateral", in which the upper arm moves laterally from a first to a second position, with the second position being spaced apart from the first and such that the longitudinal axes of the upper arm in the two positions are substantially parallel. The apparatus is adjustable, but includes two parts stationary during use; an elongate yet platelike "upper arm supporting plate" configured to be situated under the upper arm of the patient (extending proximate the armpit and extending proximate the elbow) and an elongate "forearm member" configured to be positioned proximate the forearm of the user when the user's arm is in position bent approximately 90 degrees. Two other elements cause controlled movement of the arm relative to the structure so the surgeon may perform the desired procedure. These inflatable bladders may be selectively inflated or deflated to provide a desired effect. These can be referenced as an "upper arm bladder" and a "forearm bladder", although they may be also referenced as first and second bladders, although not necessarily in that order. By inflating the upper arm bladder, the upper arm is moved away from the upper arm supporting plate, causing perpendicular (a.k.a., "lateral") force to occur to elevate the humerus perpendicularly from the glenoid to allow good clean glenoid work.

34 Claims, 19 Drawing Sheets

Y
X
S
SA
5
SECOND BLADDER 40
FIRST BLADDER 20
3
31
ELBOW E
4
LA
TENSION SLEEVE 30
48
SUPPORTING SURFACE 7

U.S. PATENT DOCUMENTS 4,370,976 A 2/1983 Wanchik et al.
4,598,701 A 7/1986 Schaefer
4,599,996 A 7/1986 Seith et al.
4,649,928 A * 3/1987 Samaras et al. ............ 600/483
4,669,451 A 6/1987 Blauth et al.
4,671,258 A 6/1987 Barthlome
4,807,606 A 2/1989 Hasegawa et al.
4,867,140 A 9/1989 Hovis et al.
4,930,523 A 6/1990 Laico et al.
4,960,115 A 10/1990 Ranciato
5,020,515 A 6/1991 Mann et al.
5,033,457 A 7/1991 Bonutti
5,056,504 A 10/1991 Mann
5,117,814 A 6/1992 Luttrell et al.
5,163,451 A 11/1992 Grellas
5,179,939 A 1/1993 Donovan et al.
5,219,324 A 6/1993 Hall
5,230,335 A 7/1993 Johnson, Jr. et al.
5,242,378 A 9/1993 Baker
5,288,286 A 2/1994 Davis
5,312,322 A 5/1994 Santana
5,313,971 A 5/1994 Upshaw
5,348,530 A 9/1994 Grim et al.
5,378,224 A 1/1995 Billotti
5,407,421 A 4/1995 Goldsmith
5,417,643 A 5/1995 Taylor
5,423,333 A * 6/1995 Jensen et al. ................ 128/878
5,425,567 A 6/1995 Albecker, III
5,445,602 A 8/1995 Grim et al.
5,453,082 A 9/1995 Lamont
5,514,081 A * 5/1996 Mann .......................... 602/20
5,514,155 A 5/1996 Daneshvar
5,542,911 A 8/1996 Cassford et al.
5,730,710 A 3/1998 Eichhorn et al.
5,916,186 A 6/1999 Turto et al.
5,938,573 A 8/1999 Davies, III et al.
5,950,628 A 9/1999 Dunfee
5,961,512 A 10/1999 Purnell
6,007,500 A 12/1999 Quintinskie, Jr.
6,113,562 A 9/2000 Bonutti et al.
6,179,800 B1 1/2001 Torrens
6,238,357 B1 5/2001 Kawaguchi et al.
6,409,691 B1 6/2002 Dakin et al.
6,572,570 B1 6/2003 Burns et al.
6,589,194 B1 7/2003 Calderon et al.
6,669,660 B2 12/2003 Branch
6,872,186 B2 3/2005 Branch et al.
2003/0130600 A1 7/2003 Branch
2004/0171973 A1 9/2004 Branch
2005/0202943 A1 9/2005 Branch et al.
2005/0222573 A1 10/2005 Branch et al.
2006/0116619 A1 6/2006 Weinstein et al.

* cited by examiner (FOREARM DIRECTED AT VIEWER ALONG "Z" AXIS)

METHOD AND APPARATUS FOR MULTIDIRECTIONAL POSITIONING OF A SHOULDER

CROSS-REFERENCE TO RELATED APPLICATIONS

This application claims priority to and the benefit of U.S. Provisional Application No. 60/561,087, filed Apr. 9, 2004, entitled “Method and Apparatus for Multidirectional Positioning of a Shoulder”, which is incorporated herein in its entirety.

FIELD OF THE INVENTION

The present invention is generally related to the manipulation of a joint such as a shoulder in order to provide surgery thereon or other medical attention thereto.

BACKGROUND OF THE INVENTION

Devices in the past have been used for the purposes of providing manipulation of a joint such as a shoulder in order to provide surgery thereon or other medical attention thereto.

One type of prior art method and apparatus is discussed with reference to FIG. 1. This prior art concept includes use of “cuff-with-cable” apparatus. As may be seen, a patient 5 has a shoulder with a rotational axis SA. From the shoulder extends an arm 6 having an upper arm extending from the shoulder and terminating at an elbow E. A forearm 4 extends from the elbow. This arm 6, which should be considered a typical human arm, is manipulated by a prior art device in FIG. 1. This device includes a cable (a.k.a., “line”) 8 and an arm grasping cuff 7. The cable 8 is maintained in tension by an external device (not shown) and pulls upon the cuff 7, which is attached to the arm 6 of the patient 5.

As may be understood, tension on the cable 8 provides a force on the arm via the sleeve in order that the arm can be pulled substantially along one of several axes: A, A', A''', etc. These axes are extended substantially through the shoulder axis SA. In the prior art, the surgeon manipulates the cable between the various axes in order to position the shoulder at a preferred orientation.

Adjustments by this prior art device can be made by 1) increasing or decreasing the tension on the cable, so as to separate the associated bones in the shoulder, and/or 2) moving (i.e., pivoting) the cable axis about the shoulder by either moving the patient or by moving the remote cable securing location.

This type of prior art manipulation of a shoulder is currently in use and has its advantages, but there are always opportunities for improvement.

SUMMARY OF THE INVENTION

The present invention provides improvements over the prior art by providing a method and apparatus for manipulating a shoulder joint in two independent directions in order to facilitate surgery thereon.

Generally described, the present invention is directed towards a method for manipulating the arm and shoulder extending from a torso of a patient, the arm of the patient including an upper arm extending from the shoulder to an elbow, and a forearm extending from the elbow to a hand, the method comprising the steps of: positioning the arm of the patient such that the longitudinal axis of the forearm is substantially at a right angle relative to the longitudinal axis of the upper arm, positioning an inflatable forearm bladder proximate to the forearm, securing the forearm bladder in place and inflating the forearm bladder so as to provide a force against the forearm so as to cause the forearm to move generally away from the forearm bladder and the upper arm of the patient to move away from the shoulder of the patient, and to cause the upper arm of the patient move substantially parallel to the longitudinal axis of the upper arm.

The invention is also directed towards a method for manipulating the arm and shoulder extending from a torso of a patient, the arm of the patient including an upper arm extending from the shoulder to an elbow, and a forearm extending from the elbow to a hand, the method comprising the steps of: positioning the arm of the patient such that the longitudinal axis of the forearm is substantially at a right angle relative to the longitudinal axis of the upper arm, positioning an inflatable forearm bladder proximate to the forearm, securing the forearm bladder in place, positioning an inflatable upper arm bladder between the torso and upper arm of the patient, securing the upper arm bladder in place so that the upper arm bladder is discouraged from moving away from the upper arm of the patient, inflating the forearm bladder so as to provide a force against the forearm so as to cause the forearm to move generally away from the forearm bladder and the upper arm of the patient to move away from the shoulder of the patient, and to cause the upper arm of the patient move substantially parallel to the longitudinal axis of the upper arm, and inflating the upper arm bladder so as to provide a force against the upper arm of the patient so as to cause the upper arm to move generally away from the upper arm bladder and so as to elevate the humerus of the patient perpendicularly and away from the glenoid of the patient.

Finally, the invention is also directed towards an apparatus for manipulating the arm and shoulder extending from a torso of a patient positioned on a support surface, the arm of the patient including an upper arm extending from the shoulder to an elbow, and a forearm extending from the elbow to a hand, the apparatus comprising: a frame member assembly configured for being positioned relatively stationary relative to the support surface, a structural upper arm support member attached relative to the frame member, a structural forearm support member attached relative to the structural upper arm member and configured to be positioned proximate the forearm when the arm is bent at the elbow, a forearm retention member configured to pass around and at least partially contain the forearm and the structural forearm support member, and a forearm bladder member configured to be positioned relative to the forearm support member, the forearm retention member, and the forearm of the patient such that inflation of the forearm bladder member tends to place the forearm retention member in tension and to cause the forearm to be moved towards the structural forearm support member, such that the upper arm is moved substantially along its longitudinal axis and away from the shoulder joint as the forearm bladder member is inflated, and an upper arm bladder member configured to be positioned between the upper arm and the structural upper arm member, such that inflation of the upper arm bladder member tends to cause the upper arm bladder member to provide opposing forces on the upper arm and the structural upper arm support member, such that the upper arm is urged laterally relative to its longitudinal axis as the upper arm bladder member is inflated so as to cause the upper arm to move generally away from the upper arm bladder and so as to elevate the humerus of the patient perpendicularly and away from the glenoid of the patient.

Therefore it is an object of the present invention to provide an improved medical device and technique for using same.

It is a further object of the present invention to provide an improved method and apparatus for manipulating the shoulder of a patient.

It is a further object of the present invention to provide an improved method and apparatus for manipulating the shoulder of a patient for purposes of surgery on the shoulder.

It is a further object of the present invention to provide an improved method and apparatus for manipulating the shoulder of a patient for purposes of surgery on the shoulder.

It is a further object of the present invention to provide an improved method and apparatus for manipulating the shoulder of a patient for purposes of arthroscopic surgery on the shoulder.

Other objects, features, and advantages of the present invention will become apparent upon reading the following detailed description of the preferred embodiment of the invention when taken in conjunction with the drawing and the appended claims.

DESCRIPTION OF THE DRAWINGS

FIG. 2 shows first and second bladders 20, 40, manipulating the arm of the patient 5.

FIG. 2B shows first and second bladders 20, 40, manipulating the arm of the patient 5. Reference is made back to the above-referenced provisional application, particularly to FIG. 7, to show this position, which shows the bladder positioned underneath the arm, proximate the armpit of the patient 5.

FIG. 18B illustrates the assembly itself. FIGS. 18A, C, and D illustrate exemplary uses of the bladder and strap assembly 200.

DETAILED DISCUSSION OF THE PRESENT EMBODIMENT

Figure 1:
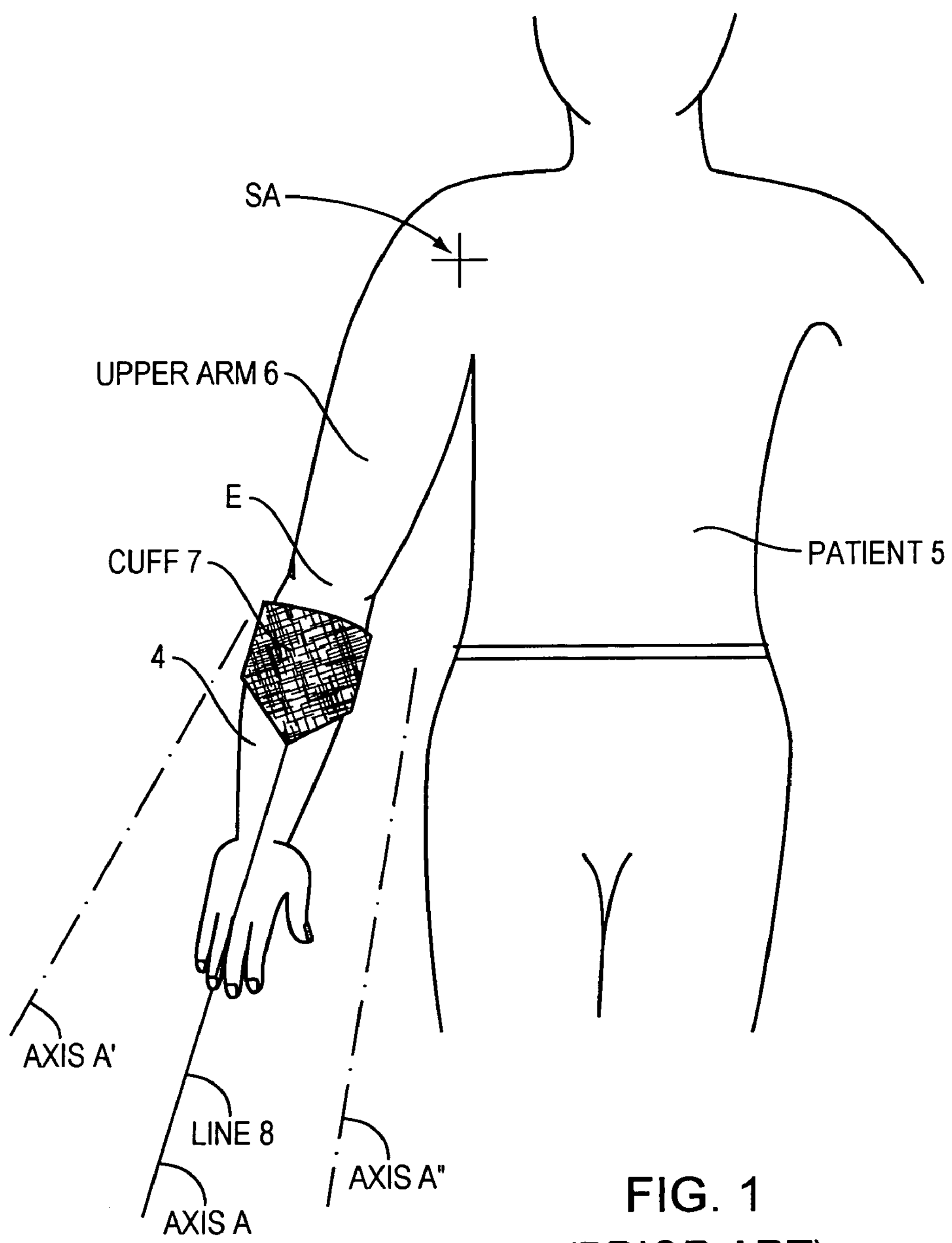
FIG. 1 illustrates a prior art method and apparatus.

Here follows a discussion of the present invention in which like numerals indicate like elements throughout the several views.

General Construction and Operation

Generally described, the invention relates to a method and apparatus for manipulating a shoulder joint, by manipulating the upper arm independently in two directions to facilitate surgery on the shoulder. The first direction of movement is a "longitudinal" movement, wherein movement of the upper arm is done substantially along the longitudinal axis of the upper arm. The second direction is a "lateral" direction, in which the upper arm moves laterally from a first lateral position to a second lateral position. The longitudinal axis of the upper arm in the first lateral position is spaced apart and substantially parallel to the longitudinal axis of the upper arm when in the second lateral position.

Stated differently, the present invention allows the shoulder to be cradled during surgery while an inflatable bladder is blown up, causing a perpendicular (a.k.a., "lateral") force to occur to elevate the humerus perpendicularly from the glenoid to allow good clean glenoid work. This bladder can be deflated and another bladder inflated, pulling the arm interiorly and away from the shoulder and parallel to the glenoid. This opens up the space between the roof of the shoulder or the acromiom and the rotator cuff, facilitating rotator cuff surgery.

Reference is made to FIGS. 2A-C and 3A-B to discuss general operation of one embodiment of the invention. This figure shows a patient 5 having an arm 6 extending from the body of the patient from a shoulder S having a shoulder axis SA.

Under one embodiment of the present invention, two bladders are used to provide two types of movement of the upper arm of the patient.

A first bladder 20 is used to cause movement of the upper arm 3 of the patient along the longitudinal axis "LA" of the upper arm. This first bladder 20 is used in combination with a tension sleeve 30, which has one portion attached relative to a frame portion 48 (later defined more particularly as a "forearm supporting rod 48") of the apparatus 10. The overall apparatus is not shown in FIGS. 2A-C and 3A-B; only selected portions such as portion 48 are shown for illustrative purposes, but it should be understood that these portions of the frame, while being adjustable, are stationary unless otherwise noted during operation of the bladders.

The first bladder 20 is positioned intermediate a portion 31 of the tension sleeve 30 and the forearm 4 of the arm 6 of the patient 5. The forearm 4 of the patient is positioned between the bladder 20 and the frame portion 48 of the device 10, but the forearm preferably is in contact only with the bladder 20. As shown elsewhere, the hand of the patient may be secured proximate the end of the frame portion 48 to concentrate the movement of the arm at the elbow in response to inflation of the bladder 20.

The tension sleeve 30 may be understood to encircle the frame portion 48, forearm 4, and the first bladder 20. As the first bladder 20 is captured between the portion 31 of the tension sleeve 30 and the forearm 4, sufficient inflation of the first bladder 20 causes the portion 31 of the tension sleeve 30 and the forearm 4 to move apart. This causes tension in the tension sleeve 30. Such tension causes the forearm to move towards the frame portion 48. Such movement of the forearm pulls the upper arm of the patient away from the shoulder along the longitudinal axis LA of the upper arm.

Therefore it may be understood that by inflating the first, "forearm" bladder 20, the upper arm is pulled towards the frame portion 48, and the upper arm is pulled at the elbow in a direction away from the shoulder and substantially along the longitudinal axis of the upper arm. This opens up the space between the roof of the shoulder or the acromiom and the rotator cuff, facilitating rotator cuff surgery.

Figure 2A:
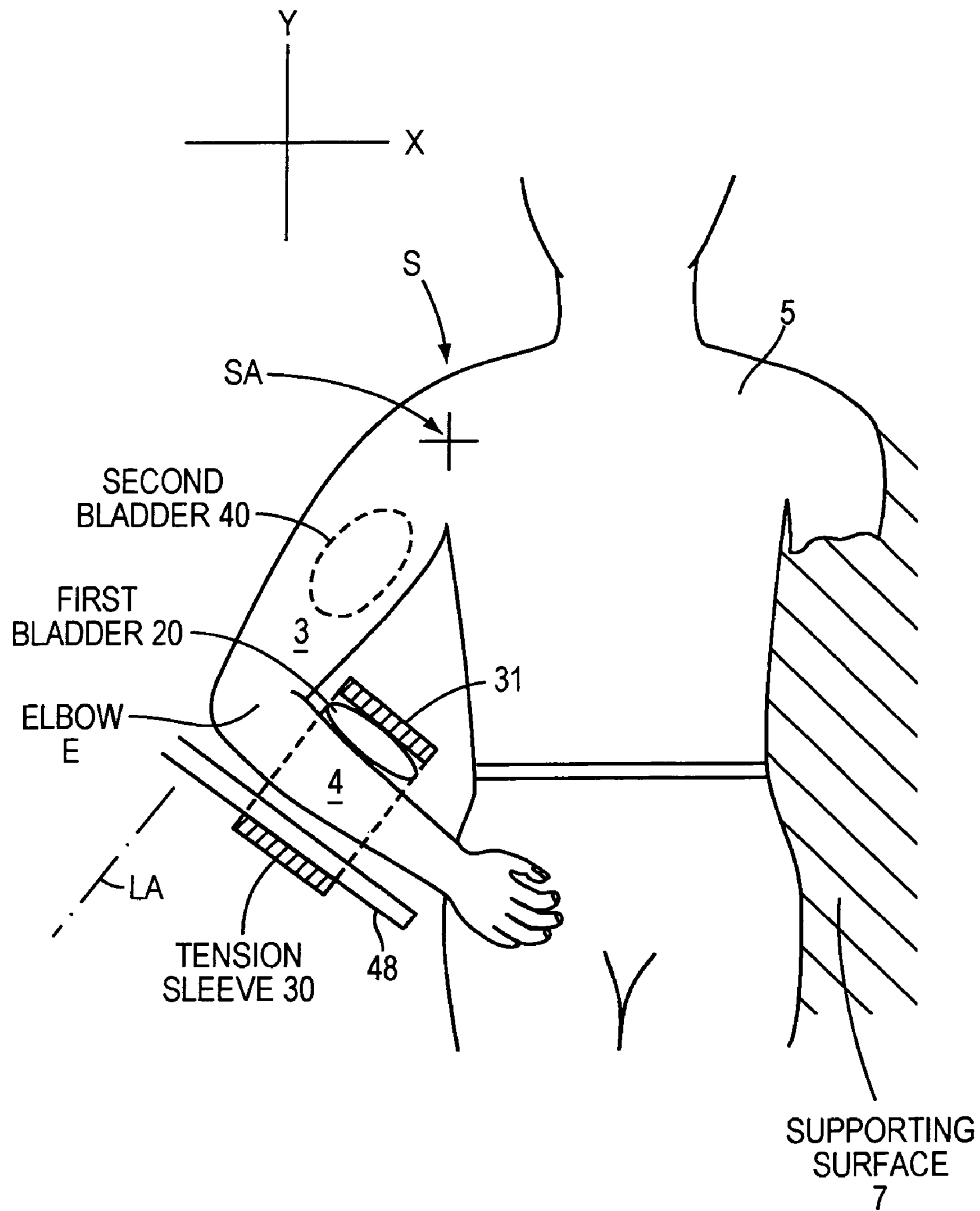
FIG. 2A is an illustrative view of a patient and a portion of the apparatus of the present invention. This view could be considered a top plan view of a patient in a prone position, looking down from above the operating table the patient is laying thereupon. As may be seen this
Figure 2B:
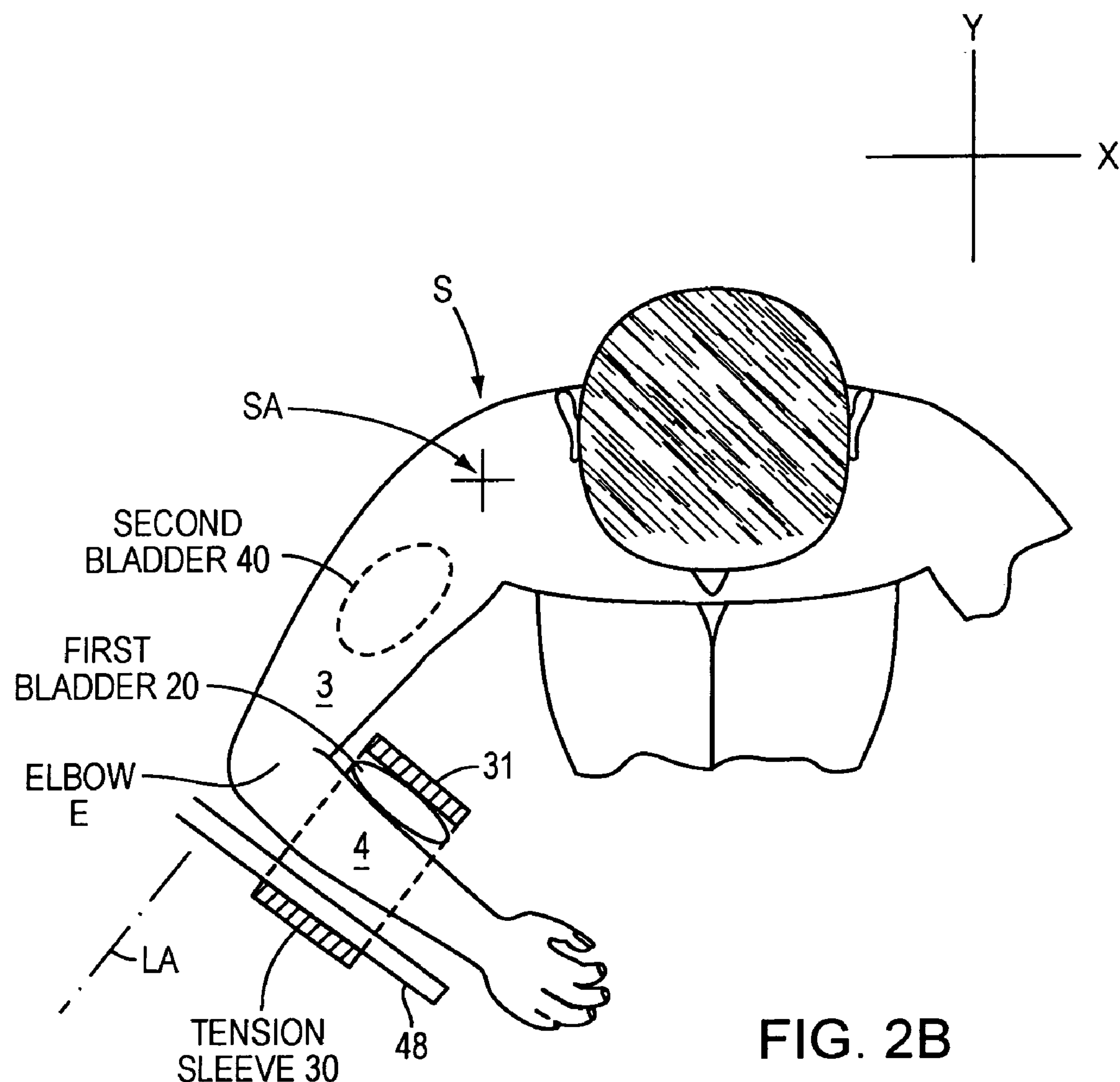
FIG. 2B is an illustrative view of a patient and a portion of the apparatus of the present invention. This view could be considered a top plan view of a patient in a sitting position, looking down from above the operating table the patient is sitting thereupon. As may be seen this

A second bladder 40 is used to cause movement of the upper arm 3 of the patient substantially transverse to the longitudinal axis "LA" of the upper arm. The upper arm 3 is positioned atop the second bladder 40, which is itself positioned atop a platelike supporting frame member 27. As may be understood, inflation of the second bladder causes opposing forces upon the upper arm and the frame member 27. As the frame member 27 is relatively fixed (although adjustable as discussed elsewhere in this application) this tends to cause the upper arm to be moved. In FIG. 2A this movement is generally towards the viewer, as FIG. 2A is viewed. This movement could be thought of as being generally in the "Z" direction, which is perpendicular to the Y and the X directions.

In FIG. 2B this movement is again generally towards the viewer, as FIG. 2B is viewed. This movement could also be thought of as being generally in the "Z" direction, which is perpendicular to the Y and the X directions.

Figure 2C:
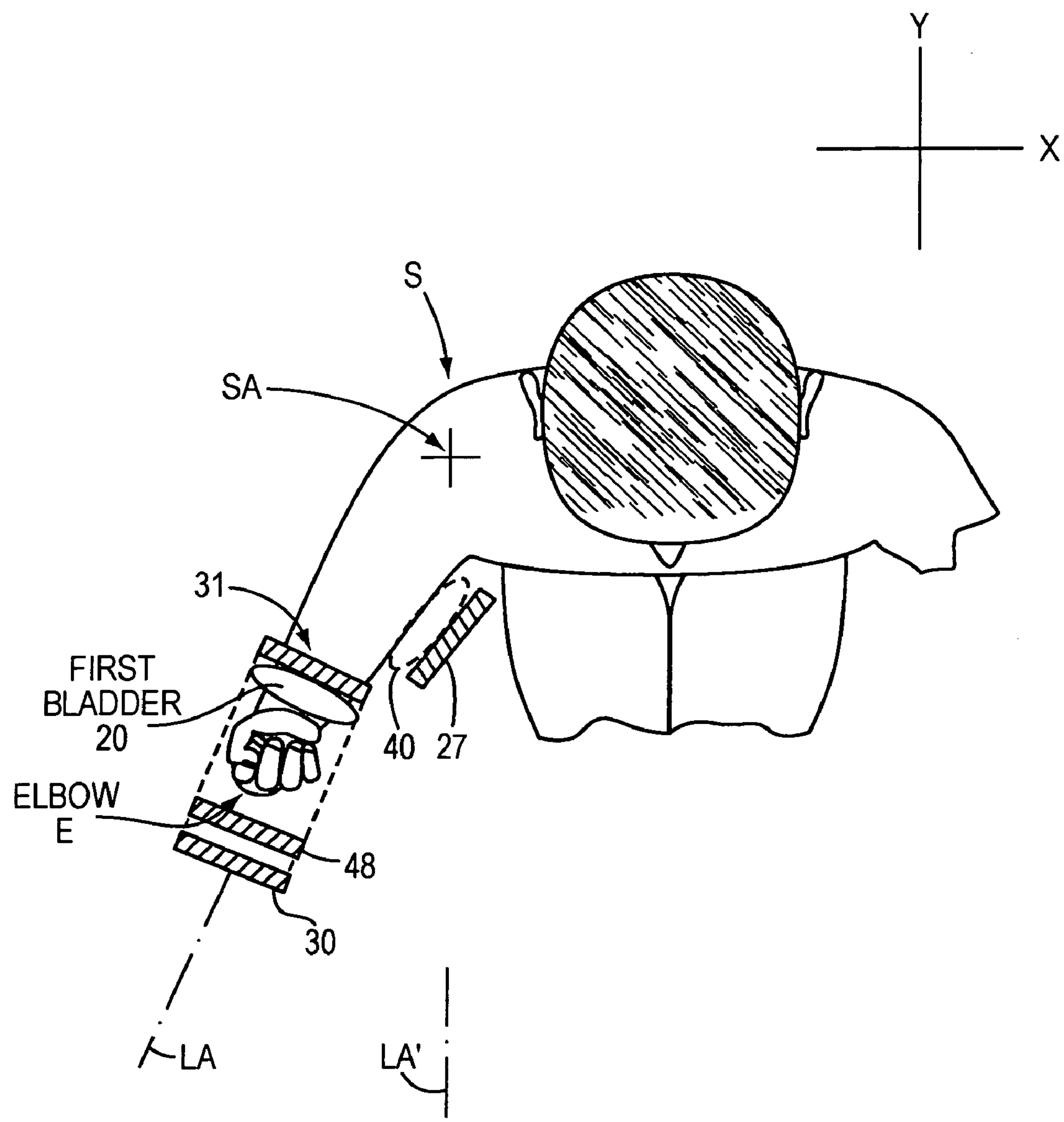
FIG. 2C is an illustrative view similar to that shown in FIG. 2B, except the patient's arm has been manipulated to rotate approximately 90 degrees about axis LA, such that the forearm of the patent is oriented with its longitudinal axis pointed substantially at the viewer, and along unshown axis "Z", which is perpendicular to shown axes X and Y. Reference is made back to the above-referenced provisional application, to FIGS. 28 and 29, for example, to also generally show this position, which shows the bladder positioned underneath the arm, proximate the armpit of the patient 5. The arm and apparatus can be manipulated as understood later such that the longitudinal axis of the arm (which passes through point SA) can be alternately positioned to position LA'. It should also be noted that the apparatus is configured in one embodiment to be attached to the portion of the bed which supports the patient's back, and thus as this portion is tilted back, so will the apparatus tilt back to suit the comfort of the patient.

In FIG. 2C this upper arm movement is again generally lateral relative to the viewer, as FIG. 2C is viewed. This movement could also be thought of as being generally in a direction lying in a plane including the X and Y axes. Note that this direction can be varied by adjustment of the apparatus, as described in detail elsewhere, such that the longitudinal axis of the upper arm is along axis LA'. It should also be understood that the apparatus can be adjusted such that the forearm can be pivoted about the LA axis, within ranges acceptable to the patient but needed by the surgeon. This pivoting movement is not normally done during the operating process, but is an adjustment prior to or between operating steps.

Figure 3A:
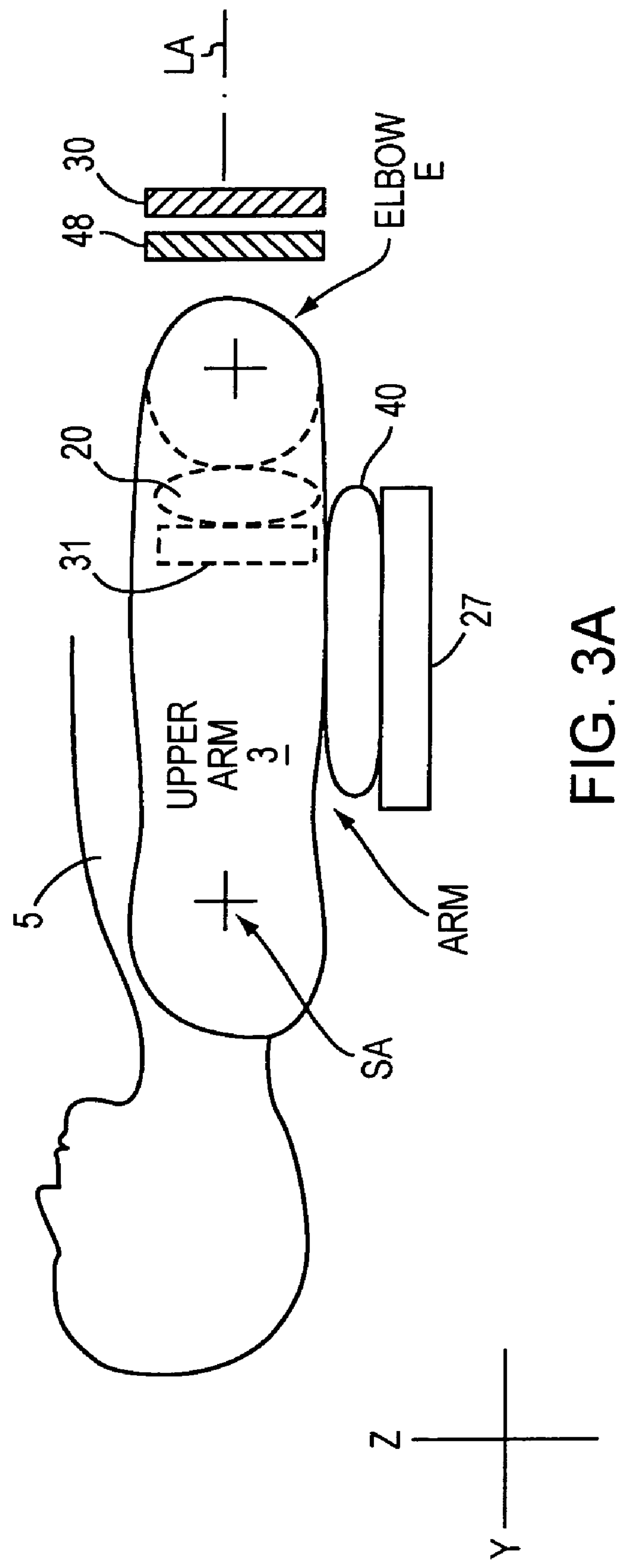
FIG. 3A is another illustrative view of a patient and a portion of the apparatus of the present invention. This view could be considered a side elevational view of a patient in a prone position, looking at the patient from the patient's right side. Again the bladders 20, 40, are shown. Structure members 27 and 48 are also shown which will be identified later as a supporting plate 27 and a forearm supporting rod 48, respectively.

In FIG. 3A this upper arm movement is generally lateral relative to the viewer, as FIG. 3A is viewed. This movement could also be thought of as being generally in the "Z" direction, which is perpendicular to the Y and the X directions.

Figure 3B:
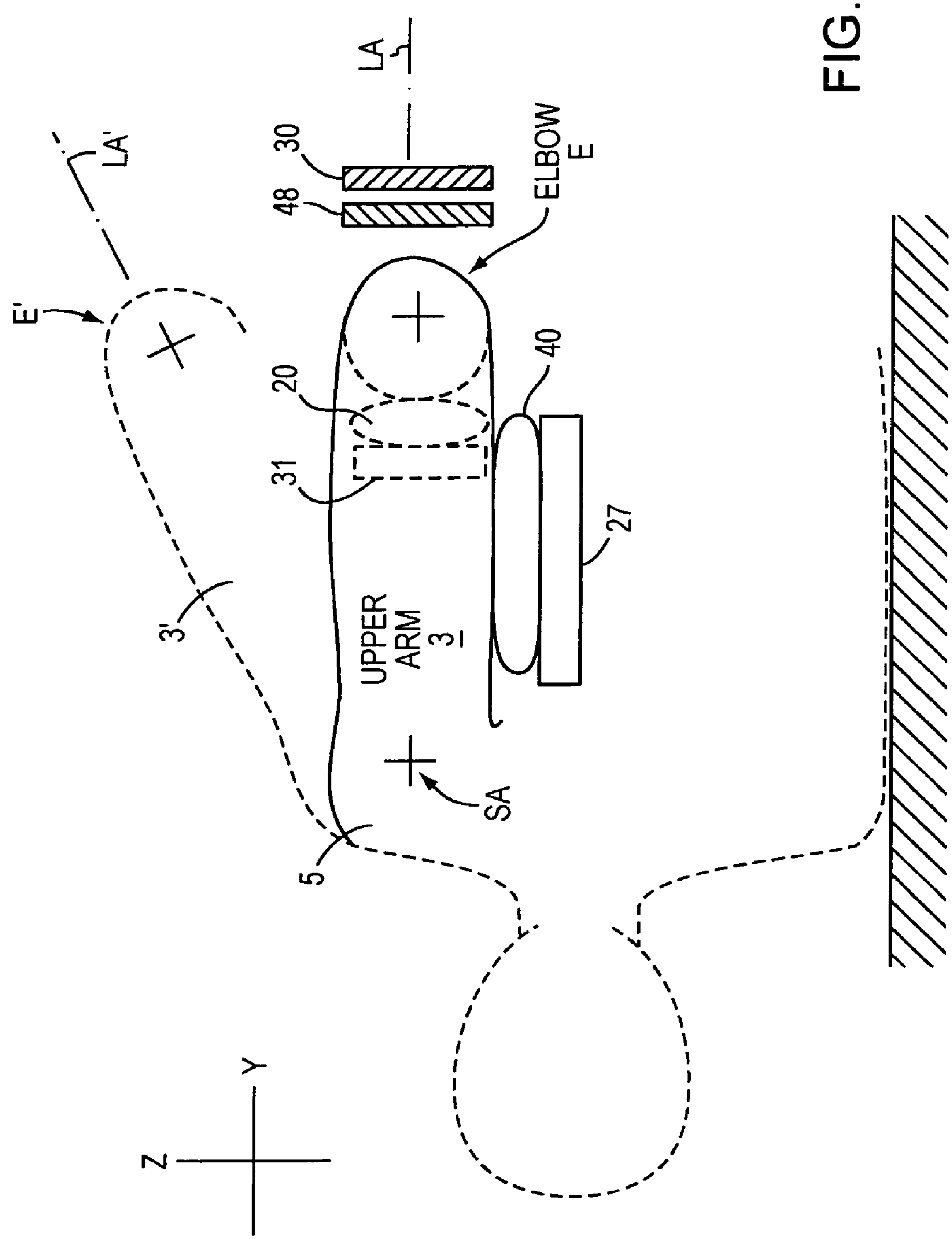
FIG. 3B is another illustrative view of a patient and a portion of the apparatus of the present invention, except the patient has been moved onto the patient's left side facing away from the viewer. This view could be considered a side elevational view of the patient, looking at the patient's back. Again the bladders 20, 40, are shown. Structure members 27 and 48 are also shown which will be identified later as a supporting plate 27 and a forearm supporting rod 48, respectively. Note again that the arm and apparatus can be manipulated as understood later (although not typically during surgical procedures, but possibly before or between them) such that the longitudinal axis of the arm can be alternately positioned to position LA', which may be more comfortable for the user as it provides more room for the items 40, 27, which are essentially under the armpit and between the upper arm and the side of the patient.

In FIG. 3B this upper arm movement is also generally lateral relative to the viewer, as FIG. 3B is viewed. This movement could also be thought of as being generally in the "Z" direction, which is perpendicular to the Y and the X directions, when the setting for the device is such that the upper arm longitudinal axis is at LA. However, as noted above, the arm and apparatus can be manipulated as understood later such that the longitudinal axis of the arm can be alternately positioned to position LA', which may be more comfortable for the user as it provides more room for the items 40, 27, which are essentially under the armpit and between the upper arm and the side of the patient. In this case, movement of the upper arm is still generally lateral to the viewer, but in a direction rotated slightly counterclockwise relative to the viewer.

Movement of the upper arm in this second direction can be done independently of the movement previously described in association with the first bladder. This allows for a medical procedure such as shoulder arthroscopy and other procedures necessary to repair, replace or otherwise improve the function of the shoulder. These procedures include distal clavicle resection, capsular reconstruction of the shoulder, rotator cuff repair, biceps release, repair or fenodesis and necrolysis or other nerve related ligament release.

Rigid Elements of a First Embodiment

The rigid elements of a first embodiment of the present invention will now be discussed. It should be understood that these rigid elements are intended under the present invention to be used in combination with inflatable bladders and flexible sleeves as discussed elsewhere in this application.

One embodiment of the invention is configured for use with a patient while in a generally prone position, lying on the back while having the arm raised slightly, and bent slightly at the elbow such that the forearm extends somewhat over the stomach, or lying on one side. A second embodiment, discussed later in this application, is configured for use with a patient while in a generally sitting position.

Figure 4:
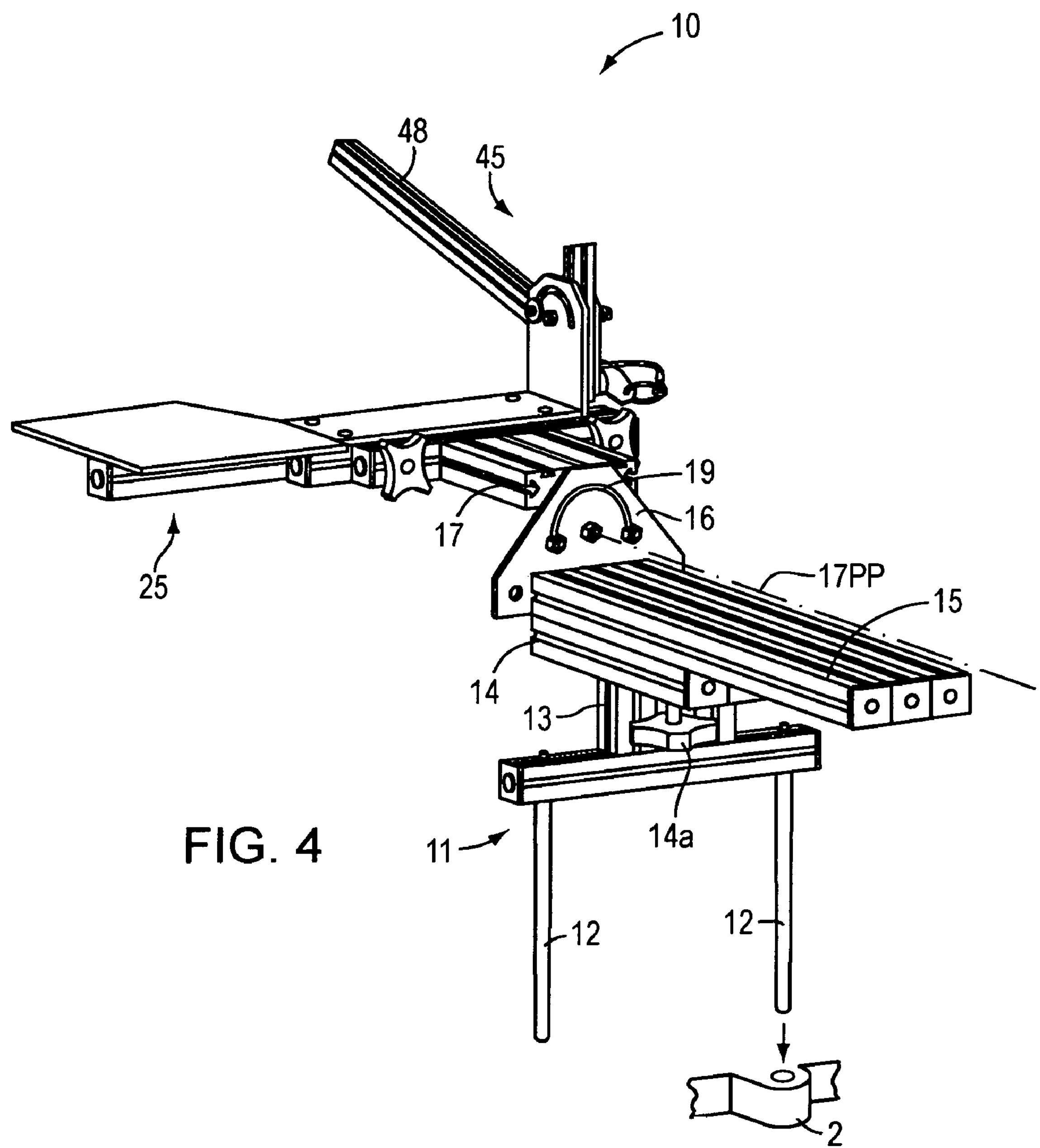
FIG. 4 is a pictorial view of the apparatus 10, including base subassembly 11, upper arm supporting subassembly 25, and forearm supporting rod subassembly 45 in accordance with an embodiment of the present invention. Reference number 2 illustrates an exemplary mounting portion of a hospital bed, to which the apparatus 10 can be attached. In one embodiment the apparatus 10 is attached to the bed which can be adjustably inclined and supports the torso of the patient.

Turning to FIG. 4, the rigid elements of the first embodiment apparatus 10 of the present invention fall into three general subassemblies: a base subassembly 11, which attaches the first embodiment apparatus 10 to an operating table, an upper arm supporting subassembly 25, which supports upper arm of patient and a forearm supporting rod subassembly 45, which supports a tension cuff and the hand of a patient.

The base subassembly 11 of the apparatus 10 includes two substantially parallel mounting rods 12 which are used to facilitate attachment of the apparatus 10 to a hospital bed. Securing the two rods together is a T-shaped connecting portion 13 rigidly attached to the rods 12 at one end. A base main portion 14 is rigidly attached to the T-shaped connecting portion 13. A generally elongate lateral adjustment member 15 is slidably attached relative to the base main portion 14, and can be adjusted along its length relative to the base main portion 14. Knobbed adjustable fasteners 14*a* releaseably fix the member 15 to the portion 14 as desired. The use of the adjustable fasteners and the sliding attachment provide for lateral adjustment of the upper arm supporting subassembly 25 in order to provide support for the upper arm or second inflatable bladder which provides a lateral force to separate the humeral head from the glenoid.

A flange 16 is attached to the interior end of the lateral adjustment member 15 and provides an attachment surface for elongate pivoting member 17. Pivoting member 17 has its longitudinal axis generally transverse to the operating table and pivots by virtue of the flange 16 about an axis offset but generally parallel to the longitudinal axis of the pivoting member 17. This pivoting feature provides for pivoting adjustment of the upper arm supporting subassembly 25 in order to provide adjustment for the angle between the body and the upper arm. A guide pin 19 fits within an arcuate slot defined by the flange 16 and acts as a guide and a stop.

Figure 5:
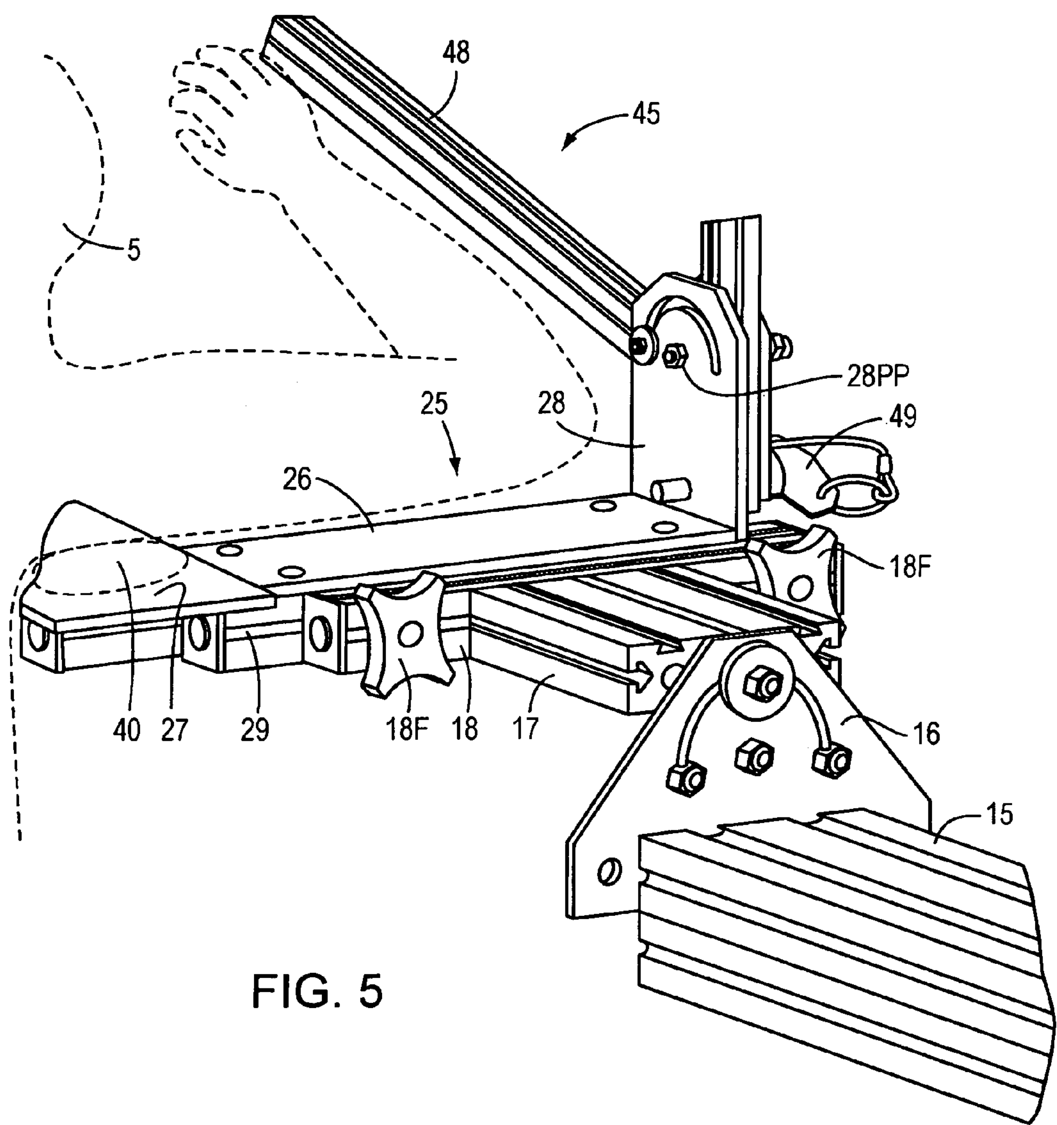
FIG. 5 is a partial view of the first embodiment apparatus 10 according to an embodiment of the present invention. This shows the relative positioning of the upper arm supporting subassembly 25 relative to the mounting bar 18. Shown in phantom line is an exemplary patient 5, such as shown in FIG. 7 of the above-referenced provisional application, with a bladder 40 shown in phantom as well. The viewer is looking at the patient's back with the right arm of the patient being manipulated; the patient could be standing or sitting.

Referring to FIG. 5, a carriage mounting bar 18 is mounted in a perpendicular orientation relative to the interior end of the pivoting member 17. This mounting bar 18 includes two mounting fasteners 18f which provide for releasable and adjustable mounting of the base assembly 11 to the upper arm supporting assembly 25 as described elsewhere in this application. These mounting features each include adjustment knobs, which can be grasped by a human hand and twisted. Depending on the direction of the twist, this causes the carriage-bolt-type heads of the fasteners to tighten or loosen their fit within a cooperating channel 29 defined by the upper arm supporting subassembly 25. It may be understood that the bolt heads are not shown in the figures as they are concealed within the channel.

The upper arm supporting subassembly 25 is attached to the base subassembly 11 through a sliding connection which facilitates its adjustment relative to the base portion in a direction generally parallel to the longitudinal axis of the elongate mounting bar 18 described above. The upper arm supporting subassembly 25 includes a base member 26, an upper arm supporting plate 27, and a flange 28. The base member 26 is adjustably attached to carriage mounting bar 18 and the upper arm supporting plate 27 is mounted proximate to what could be said to be the “head” end of the somewhat elongate base member 26. The upper arm supporting plate 27 supports the second bladder as discussed in detail elsewhere. The supporting plate 27 is slidably mounted relative to the base member 26, but when in use it is typically fixed in place. A flange 28 is rigidly attached to what could be said to be the “foot” end of the base member. In other words, the flange 28 is attached to the base member end that is opposite the end to which the upper arm supporting plate 27 is attached. This flange 28 pivotably supports the forearm supporting rod subassembly 45, discussed immediately below.

Figure 6:
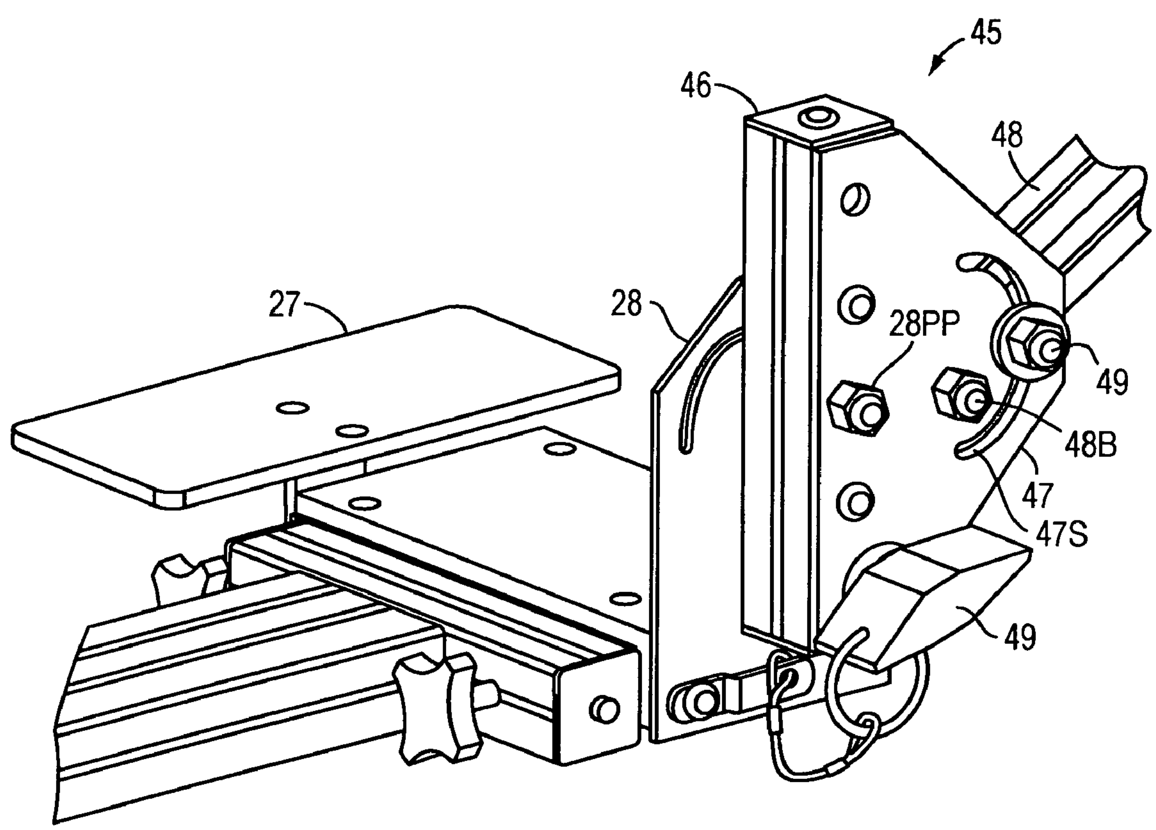
FIG. 6 is a partial "reverse angle" view relative to that shown in FIG. 5, particularly the forearm supporting rod subassembly 45 shown in a "right arm setup" mode.
Figure 7:
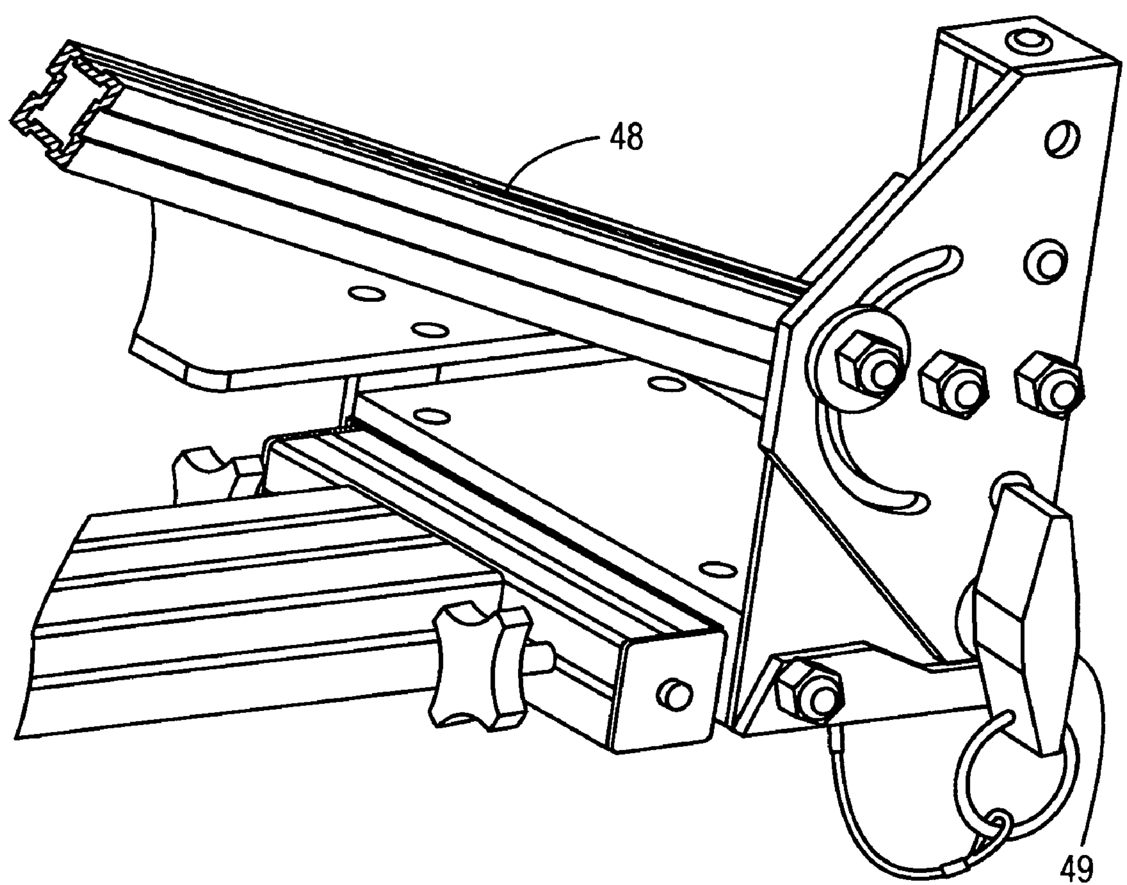
FIG. 7 is a view similar to that of FIG. 6, except the forearm supporting rod subassembly 45 is in a "left arm setup" mode.

The forearm supporting rod subassembly 45 is configured to provide a structural member towards which the forearm can be pulled via use of the tension sleeve 30 as generally illustrated in FIG. 2. This assembly 45 is attached to the upper arm supporting subassembly 25 through a pivoting connection about a pivot point 28PP, which allows for the surgeon to adjust the assembly to facilitate treatment on the left or right arm of the patient. This assembly is held in place with a locking pin 49 as generally shown in FIGS. 6 and 7. This subassembly 45 includes the following elements: a short frame member 46 pivotably attached relative to the flange 28 proximate pivot point 28PP, a flange 47 rigidly mounted to the short frame member 46.

Turning briefly to FIGS. 6 and 7, the forearm supporting rod 48 is pivotably mounted via bolt 48B to the flange 47 and has a slot-following fastener 49 extending through the rod 48 and also through an arcuate slot 47S in the flange 47. Pivoting of the rod 48 relative to the flange 47 allows the surgeon to adjust the rotational axis of the arm relative to the shoulder. The use of a locking pin 49 allows the short frame member 46 to be pivoted between two positions, a “right arm” (FIG. 6) and a “left arm” (FIG. 7) position, as desired by the surgeon. This pin is removed, the frame member 46 is pivoted, and the pin 49 is replaced. As noted elsewhere in this application the forearm supporting rod subassembly 45 is configured to provide a structural member which the forearm can be pulled towards via use of the tension sleeve 30.

As discussed above, the base 11 of the first embodiment apparatus 10 of the invention is configured to attach to an operating table as known in the art to allow the surgeon (not shown) to manipulate the patient while in a prone position. A second base 111 in embodiment 110 discussed below is configured to allow the surgeon to operate on the patient while in a sitting position. However, as will be seen, the subassemblies 25 and 45, discussed above are configured to be used in the second embodiment as well.

Rigid Elements of a Second Embodiment

Figure 8:
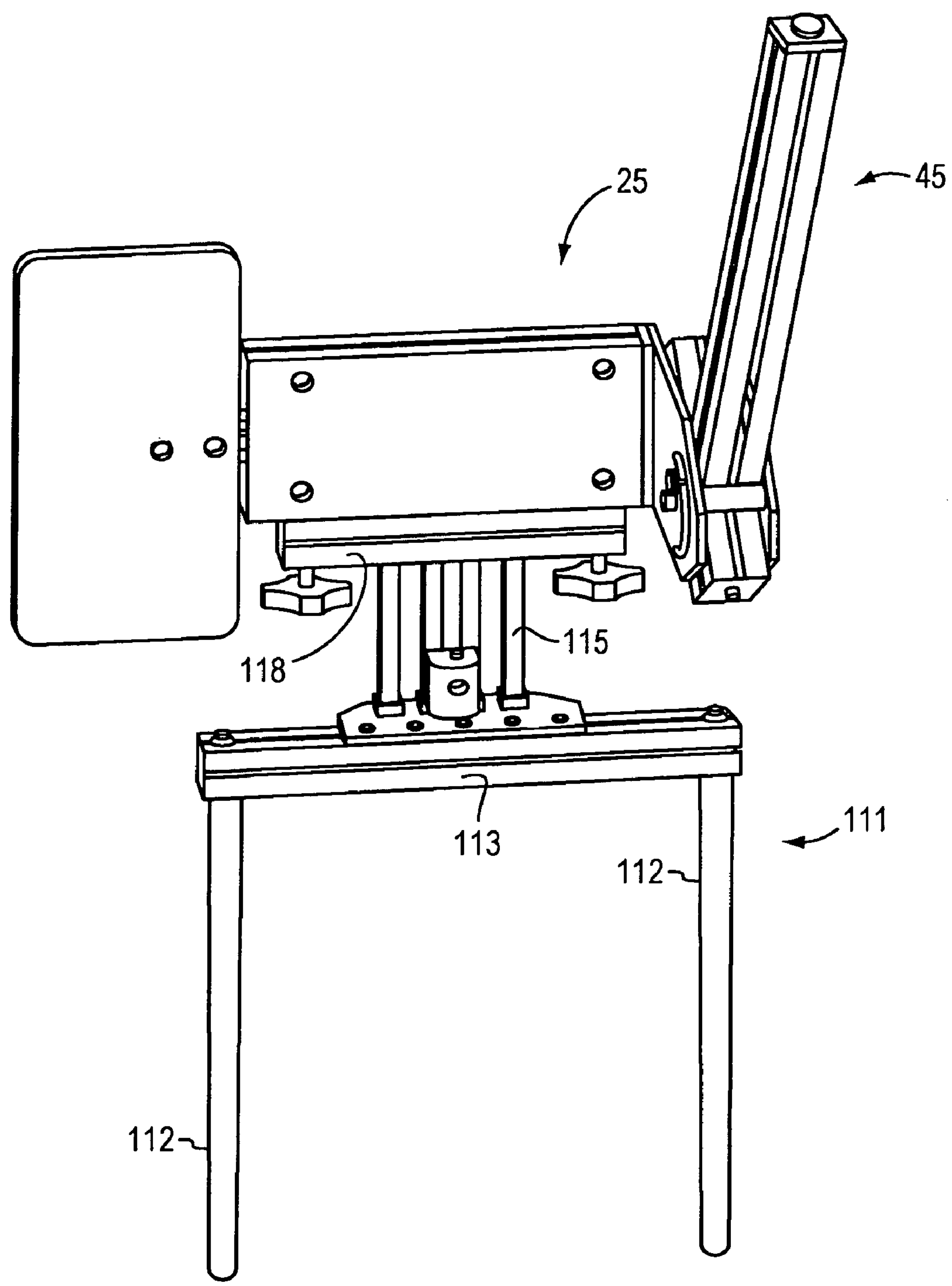
FIG. 8 is a drawing illustrating a second embodiment 110 of the present invention, including a second base subassembly 111, and elements 25, 45.
Figure 9:
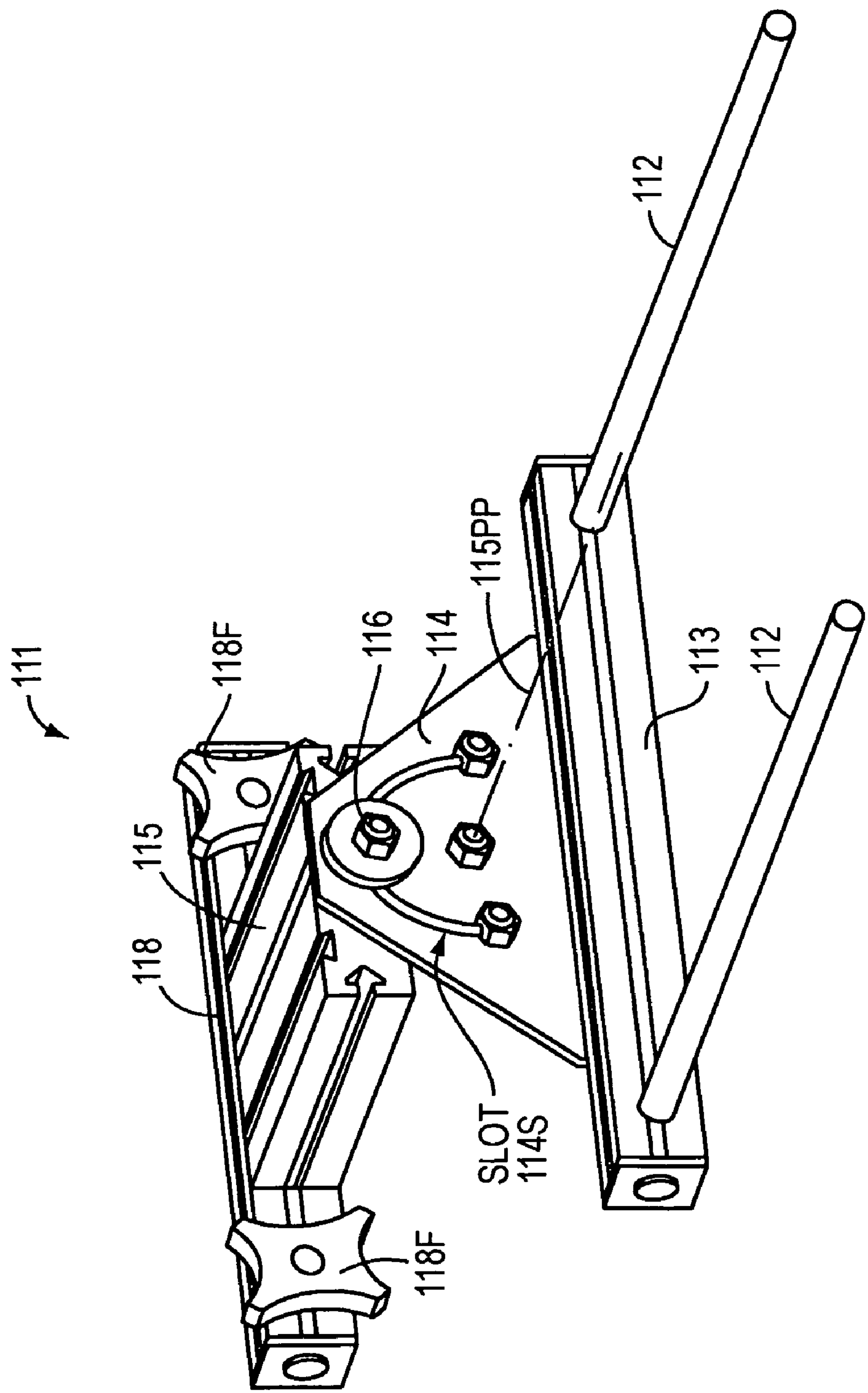
FIG. 9 is an isolated pictorial view of the second base subassembly 111.

With reference to FIGS. 8 and 9, the rigid elements of a second embodiment of the present invention will now be discussed. It should be understood that these rigid elements are configured to be used in combination with inflatable bladders as discussed elsewhere in this application. Furthermore, the second embodiment of the invention is configured for use with a patient while in a generally sitting position.

The rigid elements of the second embodiment 110 of the present invention fall into three general subassemblies: a base subassembly 111 which attaches the first embodiment 110 to an operating table, an upper arm supporting subassembly 25 that supports the upper arm of patient and a forearm supporting rod subassembly 45 that supports tension sleeve.

Referring to FIG. 9, the base subassembly 111 of the apparatus 110 includes two substantially parallel mounting rods 112 that are rigidly attached to and supported by a base main portion 113. A flange 114 is rigidly attached relative to the base main portion 113 and includes a mount support for pivot point 115PP and an arcuate slot 114S. A pivoting short member 115, which is pivotably mounted relative to the flange about an axis along pivot point 115PP, said axis being substantially parallel to the longitudinal axis of the two mounting rods 112. A follower element 116 attached to the short member 115 rides in slot 114S.

A carriage mounting bar 118 is rigidly attached to the end of the pivoting short member 115. This mounting bar 118 including mounting fasteners 118F provides for releasable and adjustable mounting of the base subassembly 111 to the upper arm supporting subassembly 25 as described elsewhere in this application, much in the same way the mounting bar 18 provides adjustable support in the first embodiment.

As noted above, the second embodiment 110 also includes upper arm supporting subassembly 25 which supports the upper arm of a patient, and the forearm supporting rod subassembly 45 which supports a tension sleeve as discussed above.

The Tension Sleeve 30

Figure 10A:
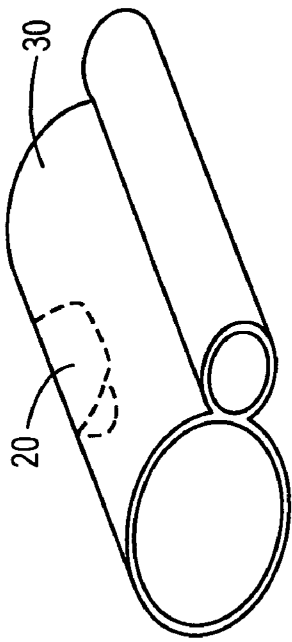
FIGS. 10A-B are pictorial and top plan views, respectively, illustrating a tension sleeve 30 in accordance with one embodiment of the present invention.
Figure 10B:
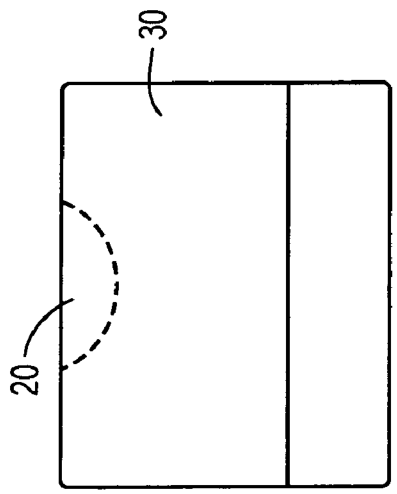

Turning to FIGS. 10A,B The first inflatable bladder in both embodiments 10, 110 of the invention may be used with a tension sleeve 30 with the sleeve encircling the structural member 48 and the forearm 4 of the patient, with the first bladder 20 being sandwiched between a portion 31 of the sleeve 30 and the forearm 4 of the patient. As noted above, inflation of the first inflatable bladder 20 causes the forearm to move toward the structural member 48, and deflation allows it to move away from the structural member. This configuration is shown illustratively in FIG. 2 and in a more commercial configuration in FIGS. 10A and B.

The Bladders 20, 40

Figure 11:
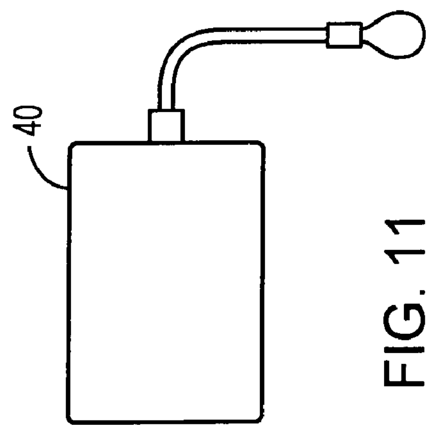
FIG. 11 is an isolated top plan view illustrating an inflatable bladder 40 in accordance with an embodiment of the present invention; this is to be used as shown in FIGS. 10A and 10B.

The bladders 20, 40, may be used in either of the embodiments 10, 110, described above. The bladders are shown illustratively in FIGS. 2 and 3. FIG. 7 shows bladder 40 in a dotted line. FIG. 11 shows an embodiment of inflatable bladder 40.

Operation of the Various Above Embodiments

As noted generally above, the invention relates to a method and apparatus for manipulating a shoulder joint, by manipulating the upper arm independently in two directions to facilitate surgery on the shoulder. The first direction of movement is a "longitudinal" movement, wherein movement of the upper arm is done substantially along the longitudinal axis of the upper arm. The second direction is a "lateral" direction, in which the upper arm moves laterally from a first lateral position to a second lateral position. The longitudinal axis of the upper arm in the first lateral position is spaced apart and substantially parallel to the longitudinal axis of the upper arm when in the second lateral position.

Stated differently, the present invention allows the shoulder to be cradled during surgery while an inflatable bladder is blown up, causing a perpendicular (a.k.a., "lateral") force to occur to elevate the humerus perpendicularly from the glenoid to allow good clean glenoid work. This bladder can be deflated and another bladder inflated, pulling the arm interiorly and away from the shoulder and parallel to the glenoid. This opens up the space between the roof of the shoulder or the acromiom and the rotator cuff, facilitating rotator cuff surgery.

Referring to FIG. 2, a patient 5 having an arm 6 extending from the body of the patient from a shoulder S having a shoulder axis SA. Under one embodiment of the present invention, two bladders are used to provide two types of movements of the upper arm of the patient. A first bladder 20 is used to cause movement of the upper arm 3 of the patient along the longitudinal axis "LA" of the upper arm. This first bladder 20 is used in combination with a tension sleeve 30, which has one portion attached relative to a frame portion 48 (a.k.a. "forearm supporting rod") of the apparatus 10.

The first bladder 20 is positioned intermediate a portion 31 of the tension sleeve 30 and the forearm 4 of the arm 6 of the patient 5. The forearm 4 of the patient is positioned between the bladder 20 and the frame portion 48 of the device 10, but the forearm preferably is in contact only with the bladder 20. The hand of the patient may be secured proximate the end of the frame portion 48 to concentrate the movement of the arm at the elbow in response to inflation of the bladder 20. The hand of the patient may be secured to the forearm supporting rod 48 by wrapping the hand and the forearm supporting rod 48 together as will be understood by those of ordinary skill in the art.

The tension sleeve 30 may be understood to encircle the frame portion 48, forearm 4, and the first bladder 20. As the first bladder 20 is captured between the portion 31 of the tension sleeve 30 and the forearm 4, sufficient inflation of the first bladder 20 causes the portion 31 of the tension sleeve 30 and the forearm 4 to move apart. This causes tension in the tension sleeve 30. Such tension causes the forearm to move towards the frame member 48. Such movement of the forearm pulls the upper arm of the patient towards away from the shoulder along the longitudinal axis LA of the upper arm.

Therefore it may be understood that by inflating the "forearm" bladder 30, the upper arm is pulled towards the forearm member, and the upper arm is pulled at the elbow in a direction away from the shoulder and substantially along the longitudinal axis of the upper arm. This opens up the space between the roof of the shoulder or the acromiom and the rotator cuff, facilitating rotator cuff surgery.

Referring now also to FIG. 3, a second bladder 40 is used to cause movement of the upper arm 3 of the patient substantially transverse to the longitudinal axis "LA" of the upper arm. The upper arm 3 is positioned atop the second bladder 40, which is itself positioned atop a platelike supporting frame member 27. As may be understood, inflation of the second bladder causes opposing forces upon the upper arm and the frame member 27. As the frame member 27 is relatively fixed (although adjustable as discussed elsewhere in this application) this tends to cause the upper arm to be moved generally upwardly as FIG. 3 is viewed. This movement could be thought of as being generally in the "Z" or vertical direction as FIG. 3 is viewed.

Movement of the upper arm in this second direction can be done independently of the movement previously described in association with the first bladder. This allows for a medical procedure such as shoulder arthroscopy and other procedures necessary to repair, replace or otherwise improve the function of the shoulder. These procedures include distal clavicle resection, capsular reconstruction of the shoulder, rotator cuff repair, biceps release, repair or fenodesis and necrolysis or other nerve related ligament release.

Alternate Configurations

Figure 12:
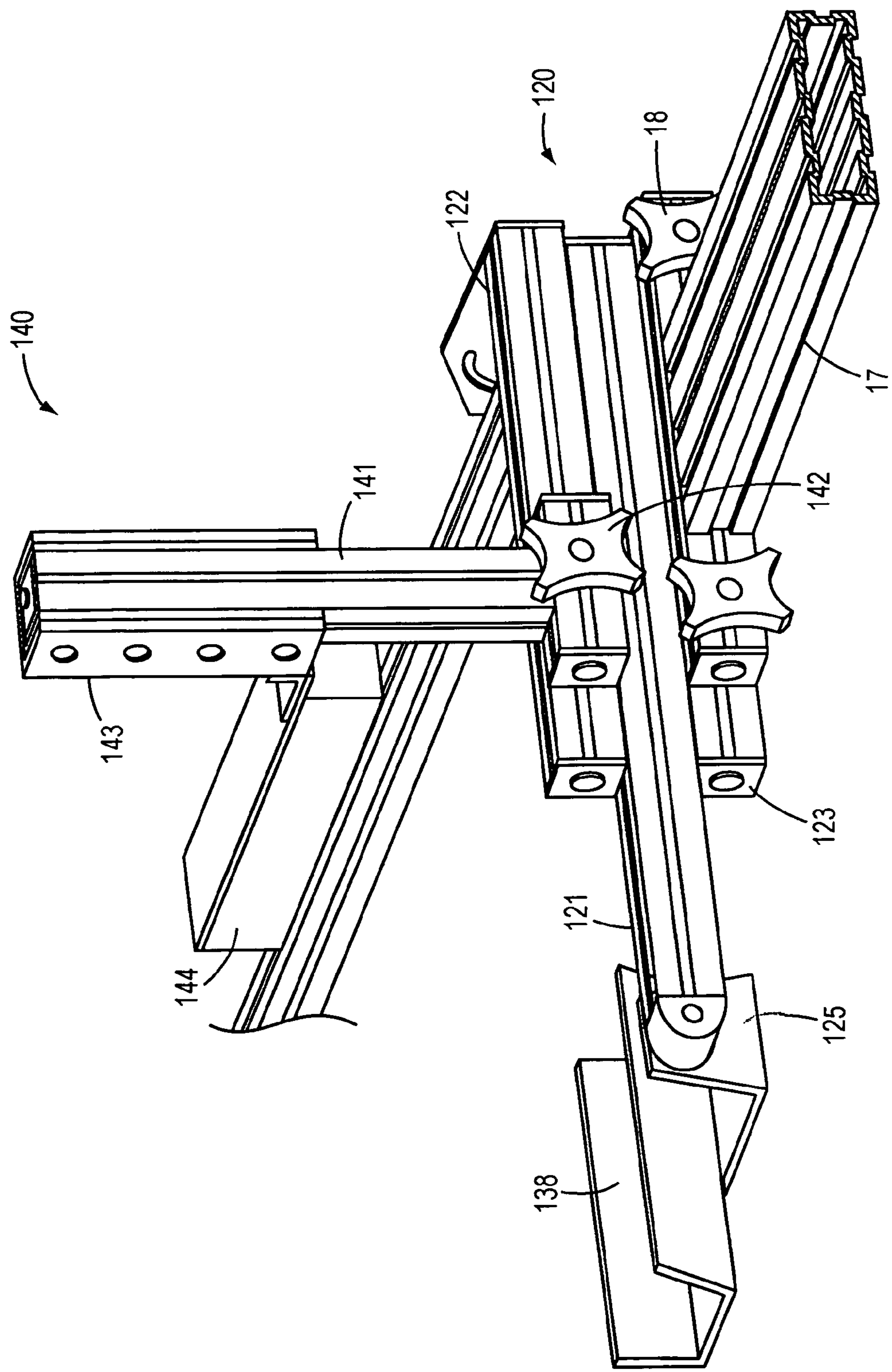
FIG. 12 is a pictorial view of an upper arm support assembly 140 in accordance with an embodiment of the present invention.
Figure 13:
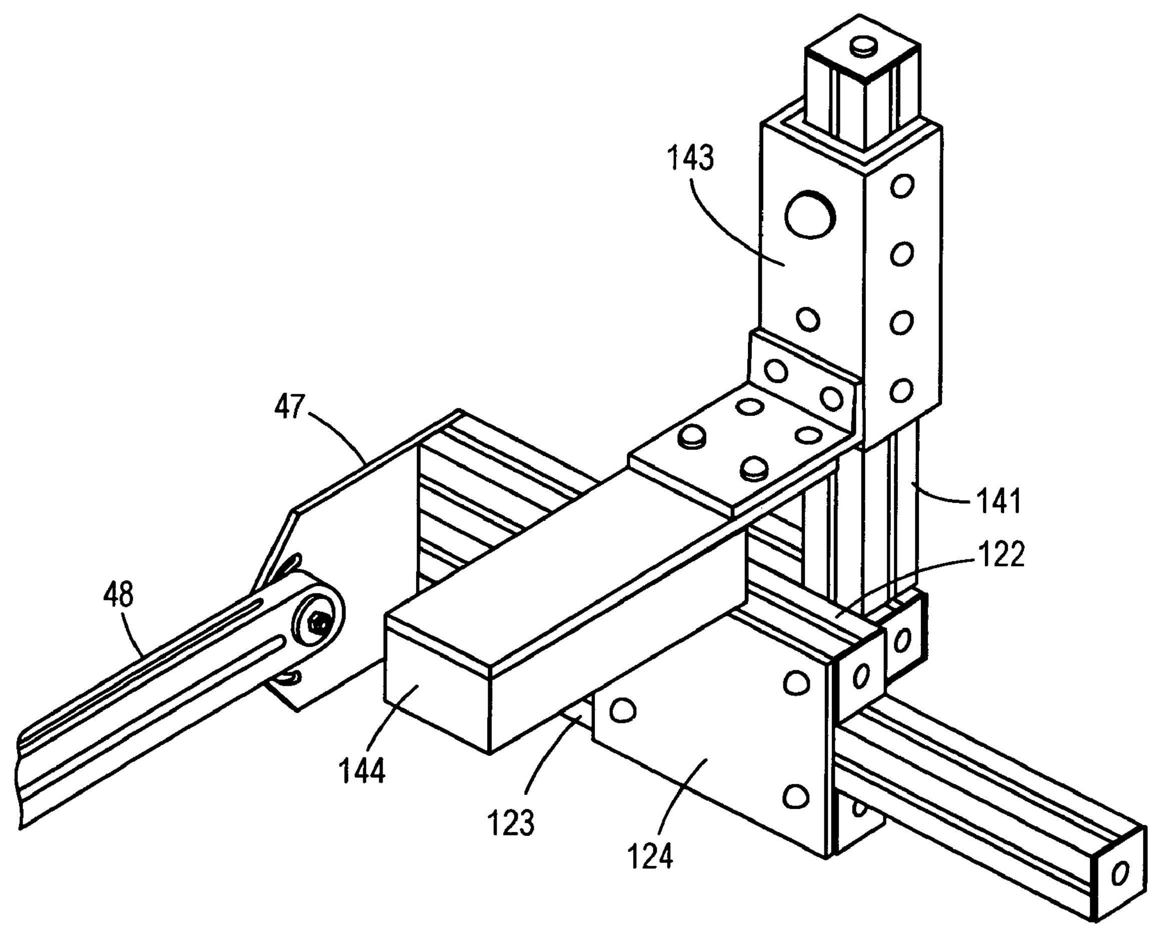
FIG. 13 is another view of that shown in FIG. 12, although element 138 is not shown.

FIGS. 12 and 13 illustrate an alternative configuration of the upper arm support assembly 25. This configuration has a base member 120 that is attached to the elongate mounting bar 18 via a sliding connection. The base member 120 is substantially perpendicular to the plane formed by pivoting member 17. This is in contrast to configurations discussed earlier in this applications where the base member 26 and the pivoting member 17 are in substantially parallel planes.

The base member 120 includes an elongate adjustment bar 121 which is intermediate an upper mounting bar 122 and a lower mounting bar 123 such that the adjustment bar 121 may move and extend out from the mounting bars 122, 123 as desired in a direction parallel to the mounting bars elongate axis. The mounting bars 122, 123 are rigidly attached to a plate bracket 124 at one end and the forearm supporting rod subassembly flange 47 at the other end as shown in FIG. 13.

Figure 14:
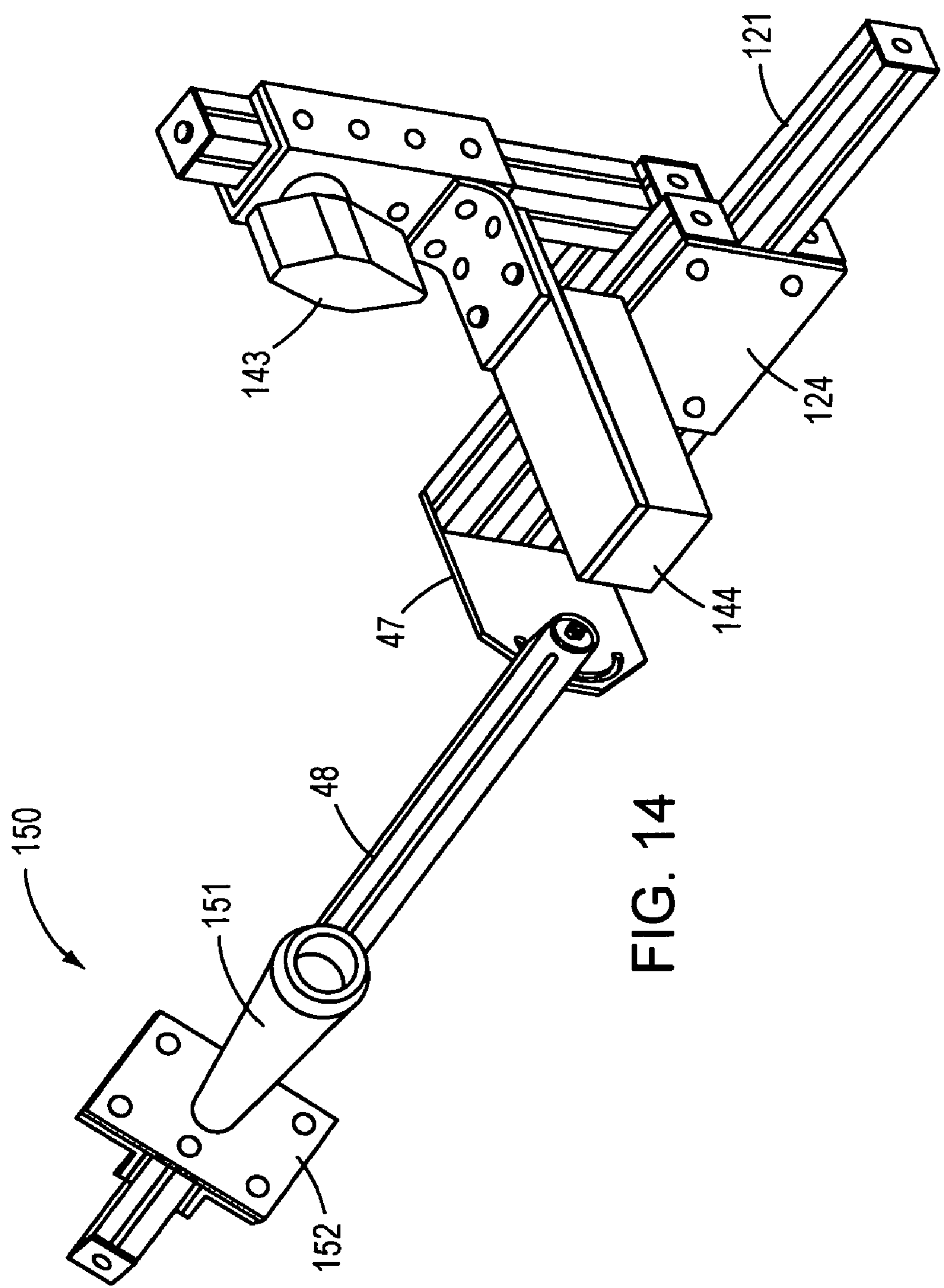
FIG. 14 is a pictorial view showing a handle assembly 150 attached to the forearm supporting rod 48. Again, element 138 is not shown.
Figure 15:
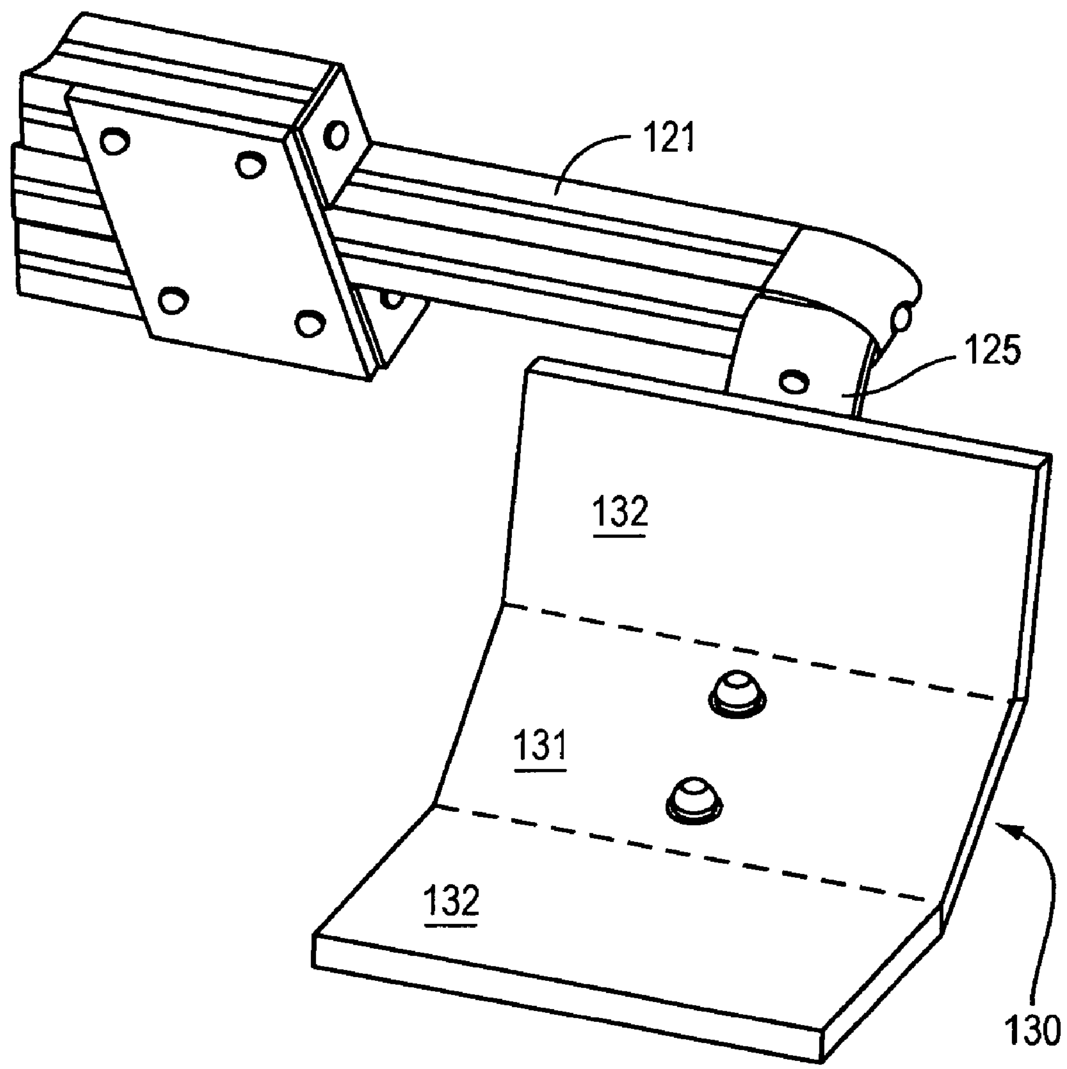
FIG. 15 is a pictorial view of the upper arm support plate 130 in accordance with an embodiment of the present invention, attached to member 121 via member 125.

Referring to FIG. 15, an offset bracket 125 is pivotably mounted to the adjustment bar 121 at the end that extends out from the mounting bars 122, 123. The support plate 138 for the upper arm is rigidly attached to the offset bracket 125. This configuration may utilize the planar upper arm support plate 27 discussed elsewhere in this application. In the configuration shown in FIGS. 12-15, the upper arm is only supported by the support plate 27 as opposed to other embodiments discussed in this application where the base member 26 also provides some support for the upper arm.

As shown in FIG. 15, the support plate 130 for this variation includes a planar base portion 131 and two lateral support portions 132, which are angled upwardly relative to the base portion at approximately 30 degrees. Dashed lines in FIG. 15 illustrate the transition areas between the base portion 131 and the two lateral support portions 132. This configuration provides support from below by the base portion 131 and lateral support by the lateral support portion 132. As one of skill in the art will recognize, the lateral support portions 132 may be formed at any angled as desired to provide lateral support.

Returning to FIGS. 12 and 13, the present invention may include an elbow support assembly 140. This assembly is positioned near the elbow and restricts the upward motion of the elbow when a bladder positioned under the upper arm is inflated. This allows the upper arm to pivot at the elbow while the bladder is inflated thereby causing the shoulder joint to separate. This separation provides access for treatment by the surgeon. The elbow support assembly includes a support column 141, an adjustable bracket 143 and a padded flange 144.

The support column 141 is generally "T" shaped with a head portion at one end and a foot portion at the opposite end. The head portion is moveably attached to the upper mounting bar 122 and provides adjustment along the length of the upper mounting bar 122. The support column 141 may be locked in place using locking knob 142, which is similar to those discussed elsewhere in this application. The foot portion of the support column is substantially perpendicular to the base member 120 and extends in a direction generally away from the upper arm of the patient.

An adjustment bracket 143 is attached to the support column 141 such that adjustment is provided at least partially along the length of the support column 141. The padded flange 144 is rigidly attached to the adjustment bracket 143 and is transverse to the upper arm of the patient. In operation, the padded flange 144 is positioned adjacent the elbow and locked into place.

An alternative configuration of the forearm supporting rod subassembly 45 is shown in FIG. 14, where a handle assembly 150 is provided to aid in securing the patient's hand to the forearm supporting rod 48. The handle assembly 150 includes a handle 151 and a carriage 152. The handle 151 has a generally cylindrical shape and extends out from the handle carriage 152 which is slidably attached to the forearm supporting rod 48 providing adjustment along the length of the forearm supporting rod 48. This feature provides a more natural hand position and facilitates retention of the hand and forearm.

Figure 16:
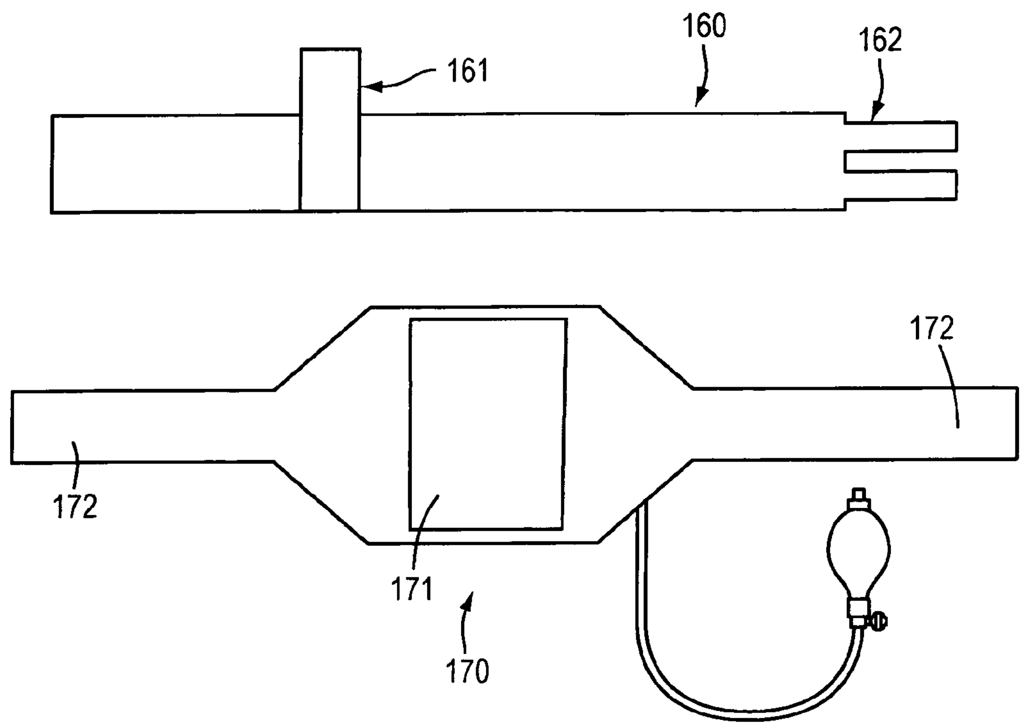
FIG. 16 is a top plan, "flattened" view of a variation of the tension sleeve comprising a retention strap 160 and a separate tension strap 170.
Figure 17:
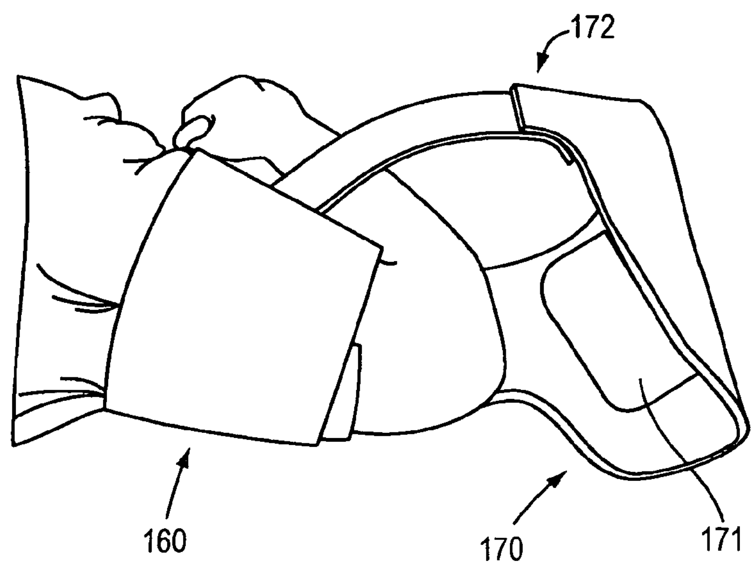
FIG. 17 is a pictorial view showing the retention strap 160 positioned about a patient's arms such that the retention tab 161 extends along the forearm.

FIGS. 16 and 17 illustrate an alternative configuration of the tension sleeve. This configuration includes an upper arm retention strap 160 and a tension strap 170. The retention strap 160 is generally rectangular with a retention tab 161 extending from one of the relatively longer sides and two fastener tabs 162 extending from one shorter "end" side. The retention strap 160 is wrapped around the patient's upper arm and secured using hook and loop fastener tabs 162 such that the retention tab 161 is adjacent the interior portion of the elbow joint and extends toward the forearm.

The tension strap 170 comprises a bladder portion 171, and two strap portions 172. The tension strap 170 is wrapped around the forearm of the patient and the forearm supporting rod (not shown) such that the forearm supporting rod 48 is intermediate the bladder portion 171 and the patient's forearm. The two strap portions 171 are connected using any convention attachment technique such as, for example, a buckle or hook and loop fasteners. Furthermore, the tension strap 170 is secured to the retention tab 161 using a hook and loop type fastener. The retention tab 161 is preferably positioned between the arm of patient and the tension straps 172. In operation, when the bladder is inflated, the forearm is urged toward the forearm supporting rod 48 due to tension on the straps 171. Because the tension strap 170 and the retention strap 160 are connected via the retention tab 161, the relative position of the upper arm and the forearm is maintained thereby concentrating the pulling force parallel to the axis of the upper arm.

FIGS. 18A-D show an alternate version of the invention without the use of an apparatus supporting the arm. A bladder and strap assembly 200 includes an inflatable bladder 201 which is positioned between the torso of the patient and the upper arm of the patient proximate the arm pit when in use. The bladder is held in place with the use of a strap 202.

Figure 18B:
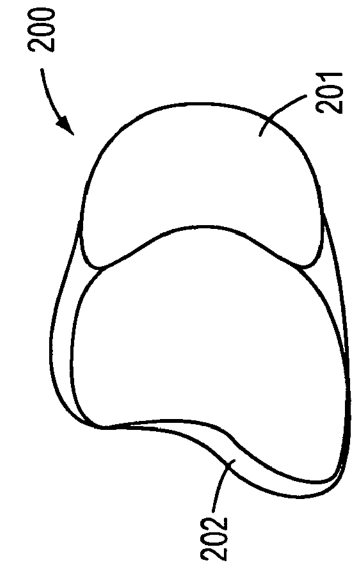
FIGS. 18A-D is several views of a bladder and strap assembly 200 in accordance with an embodiment of the present invention.
Figure 18C:
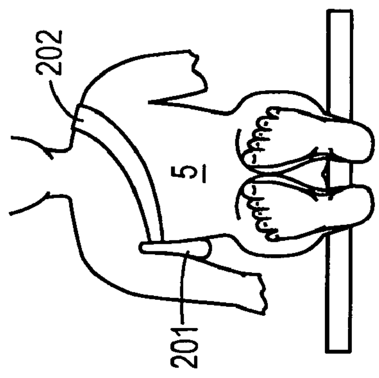
Figure 18A:
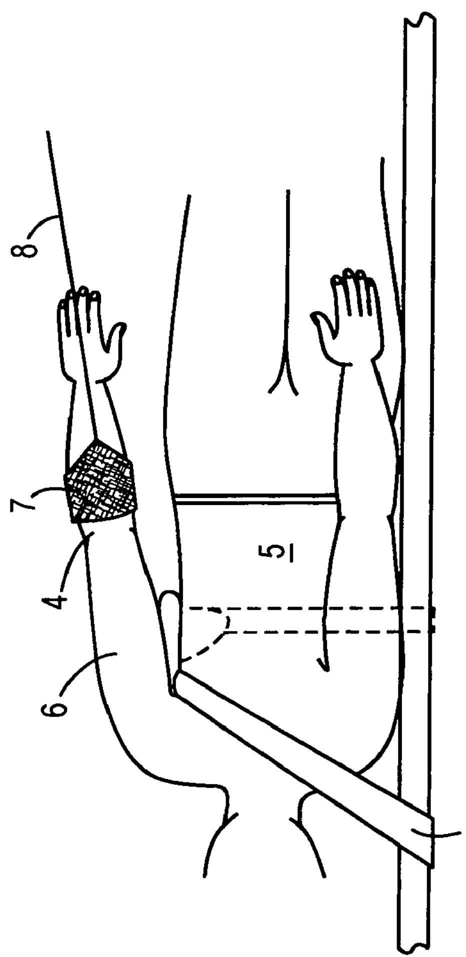
Figure 18D:
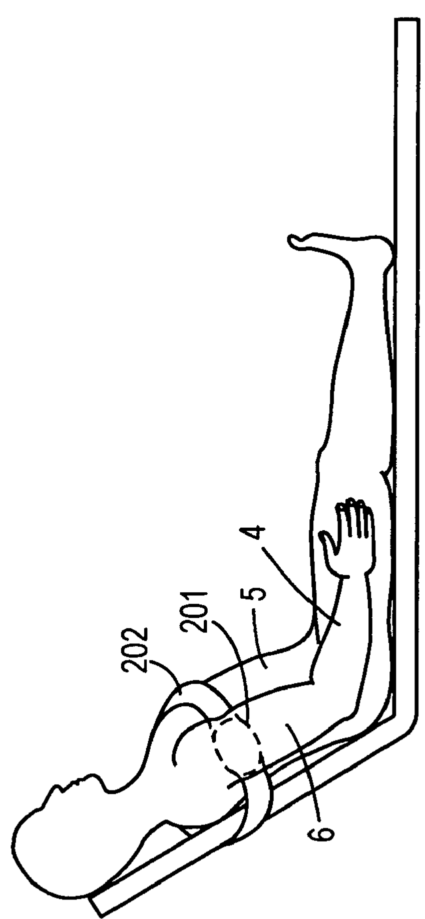

Turning specifically to FIG. 18A, this embodiment of the present invention may be used in conjunction with the prior art cuff and cable apparatus as generally shown in FIG. 1. A cuff 7 is secured adjacent the forearm 4 of the patient 5 and tension is applied to the arm of the patient along cable 8. The bladder 201 is positioned intermediate the upper arm 6 of the patient 5 and the torso of the patient and is held in place with strap 202. As will be appreciated by one of skill in the art, the strap may be oriented as desired by the surgeon for example position as shown in dotted line in FIG. 1. As illustrated, the strap 202 is secured or wrapped around the supporting surface such as a hospital bed; however, the strap may be secured over the opposite shoulder of the patient as generally shown in FIGS. 18C, D. Furthermore, this embodiment may be used with the patient in a prone, sitting or standing position. It should be understood that this embodiment of the present invention may be used without any other shoulder positioning device as generally shown in FIGS. 18C, D. The bladder 201 provides movement to the upper arm similar to the bladders described above.

It should be understood that inflation of the various bladders and adjustments to the devices can be done before, during, or after surgical procedures.

CONCLUSION

Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for manipulating an arm and shoulder extending from a torso of a patient, said arm of said patient including an upper arm extending from said shoulder to an elbow, and a forearm extending from said elbow to a hand, said method comprising the steps of:

positioning said arm of said patient such that the longitudinal axis of said forearm is substantially at a right angle relative to the longitudinal axis of said upper arm;

positioning an inflatable forearm bladder proximate to said forearm;

securing said forearm bladder relative to a frame wherein said forearm is intermediate said frame and said bladder; and inflating said forearm bladder so as to provide a force against said forearm so as to cause said forearm to move generally toward said frame thereby causing said upper arm of said patient to move away from said shoulder of said patient in a direction substantially parallel to said longitudinal axis of said upper arm.

2. A method for manipulating an arm and shoulder extending from a torso of a patient while said patient is positioned on a stationary support surface, said arm of said patient including an upper arm extending from said shoulder to an elbow, and a forearm extending from said elbow to a hand, said method comprising the steps of:

positioning said arm of said patient such that the longitudinal axis of said forearm is substantially at a right angle relative to the longitudinal axis of said upper arm;

positioning an inflatable upper arm bladder adjacent said upper arm of said patient:

securing said upper arm bladder in place relative to a substantially stationary frame;

attaching said forearm relative to said substantially stationary frame such that said forearm can rotate about an axis substantially parallel to said longitudinal axis of said forearm but is restricted from moving laterally in at least one direction relative to said longitudinal axis of said forearm; and while said patient is positioned on said stationary support surface, inflating said upper arm bladder so as to provide a first force against said upper arm of said patient, said first force being at least partially counteracted by a second force against said forearm due to its said attachment to said frame, said first and second forces combining to create a torque on said upper arm, so as to cause said upper arm and said forearm to rotate substantially about said axis substantially parallel to said longitudinal axis of said forearm such that the humerus of said patient is elevated away from the glenoid of said patient due at least in part to said torque.

3. The method as claimed in claim 2, wherein said step of attaching said forearm relative to said frame includes the use of a sleeve configured to pass around and at least partially contain said forearm such that said forearm can rotate about said axis substantially parallel to said longitudinal axis of said forearm.

4. A method for manipulating an arm and shoulder extending from a torso of a patient, said arm of said patient including an upper arm extending from said shoulder to an elbow, and a forearm extending from said elbow to a hand, said method comprising the steps of:

positioning said arm of said patient such that the longitudinal axis of said forearm is substantially at a right angle relative to the longitudinal axis of said upper arm;

positioning an inflatable forearm bladder proximate to said forearm;

securing said forearm bladder relative to a frame;

positioning an inflatable upper arm bladder between said torso and upper arm of said patient;

securing said upper arm bladder relative to said frame;

inflating said forearm bladder so as to provide a force against said forearm so as to cause said forearm to move generally toward said frame to cause said upper arm of said patient to move away from said shoulder of said patient in a direction substantially parallel to said longitudinal axis of said upper arm; and inflating said upper arm bladder so as to provide a force against said upper arm of said patient so as to cause said upper arm to move generally away from said torso so as to elevate the humerus of said patient away from the glenoid of said patient.

5. An apparatus for manipulating an arm and shoulder extending from a torso of a patient positioned on a support surface, said arm of said patient including an upper arm extending from said shoulder to an elbow, and a forearm extending from said elbow to a hand, said apparatus comprising:

a frame member assembly configured for being positioned relatively stationary relative to said support surface;

a structural upper arm support member attached relative to said frame member assembly;

a structural forearm support member attached relative to said structural upper arm member and configured to be positioned proximate said forearm when said arm is bent at said elbow;

a forearm retention member configured to pass around and at least partially contain said forearm and said structural forearm support member; and a forearm bladder member configured to be positioned relative to said forearm support member, said forearm retention member, and said forearm of said patient such that inflation of said forearm bladder member tends to place said forearm retention member in tension and to cause said forearm to be urged towards said structural forearm support member, such that said upper arm is moved substantially along the longitudinal axis of said upper arm and away from said shoulder joint as said forearm bladder member is inflated.

6. The apparatus as claimed in claim 5, wherein said forearm bladder member is a sleeve encircling a portion of said forearm and said forearm support member, and wherein said forearm bladder member is positioned between a portion of said sleeve and a portion of said forearm, such that inflation of said sleeve causes said bladder member to push relatively against said forearm to cause said forearm and upper arm movement.

7. The apparatus as claimed in claim 5, wherein said forearm retention member is a sleeve encircling a portion of said forearm and said forearm support member, and wherein said forearm bladder member is positioned between a portion of said sleeve and a portion of said forearm support member, such that inflation of said forearm bladder causes said forearm bladder member to push relatively against said forearm support member to cause said sleeve to pull on said forearm to cause said forearm and upper arm movement.

8. The apparatus as claimed in claim 5, wherein said forearm retention member is adjustable relative to said upper arm support member along an axis substantially parallel to the longitudinal axis of said upper arm, such that different forearm positions may be provided as needed.

9. The apparatus of claim 5 further comprising an upper arm cuff having a retention tab, said upper arm cuff configured to encircle said upper arm proximate said elbow such that said retention tab is secured relative to said forearm retention member so as to discourage movement of said forearm retention member in a direction substantially parallel to the longitudinal axis of said forearm.

10. The apparatus of claim 9, wherein said retention tab is secured to said forearm retention member using a hook and loop fastener.

11. The apparatus as claimed in claim 5, further comprising a handle member attached relative to said forearm support member to allow said patient to grasp said handle member with said hand of said patient.

12. An apparatus for manipulating an arm and shoulder extending from a torso of a patient positioned on a support surface, said arm of said patient including an upper arm extending from said shoulder to an elbow, and a forearm extending from said elbow to a hand, said apparatus comprising:

a frame member assembly configured for being positioned relatively stationary relative to said support surface;

a structural upper arm support member attached relative to said frame member assembly;

a structural forearm support member attached relative to said structural upper arm support member and configured to be positioned proximate said forearm when said arm is bent at said elbow;

a forearm retention member configured to pass around and at least partially maintain said forearm and said structural forearm support members in an adjacent position; and an upper arm bladder member configured to be positioned between said upper arm and said structural upper arm member, such that inflation of said upper arm bladder member tends to cause said upper arm bladder member to provide opposing forces on said upper arm and said structural upper arm support member, such that said upper arm is urged laterally relative to the longitudinal axis of said upper arm as said upper arm bladder member is inflated, so as to cause said upper arm to move generally away from said structural upper arm support member and so as to elevate the humerus of said patient away from the glenoid of said patient.

13. The apparatus of claim 12, the upper arm support member is pivotably attached relative to said frame member and configured to releasably secure said upper arm at a desired angle with reference to the longitudinal axis of said torso.

14. The apparatus of claim 12 further comprising a handle member moveably attached relative to said structural forearm support member wherein said handle may be grasped by the patient's hand.

15. An apparatus for manipulating an arm and shoulder extending from a torso of a patient positioned on a support surface, said arm of said patient including an upper arm extending from said shoulder to an elbow, and a forearm extending from said elbow to a hand, said apparatus comprising:

a frame member assembly configured for being positioned relatively stationary relative to said support surface;

a structural upper arm support member attached relative to said frame member assembly;

a structural forearm support member attached relative to said structural upper arm member and configured to be positioned proximate said forearm when said arm is bent at said elbow;

a forearm retention member configured to pass around and at least partially contain said forearm and said structural forearm support member; and a forearm bladder member configured to be positioned relative to said forearm support member, said forearm retention member, and said forearm of said patient such that inflation of said forearm bladder member tends to place said forearm retention member in tension and to cause said forearm to be moved towards said structural forearm support member, such that said upper arm is moved substantially along the longitudinal axis of said upper arm and away from said shoulder joint as said forearm bladder member is inflated; and an upper arm bladder member configured to be positioned between said upper arm and said structural upper arm member, such that inflation of said upper arm bladder member tends to cause said upper arm bladder member to provide opposing forces on said upper arm and said structural upper arm support member, such that said upper arm is urged laterally relative to said longitudinal axis of said upper arm as said upper arm bladder member is inflated, so as to cause said upper arm to move generally away from said structural upper arm support member and so as to elevate the humerus of said patient generally perpendicularly relative to the upper arm axis and away from the glenoid of said patient.

16. The apparatus of claim 15, wherein said forearm bladder member and said upper arm bladder member are independently controllable.

17. The apparatus of claim 15 further comprising an elbow support member positioned proximate the elbow of said patient configured to restrict upward movement of the elbow when said upper arm bladder member is inflated.

18. The apparatus of claim 15, the upper arm support member is pivotably attached relative to said frame member and configured to releasably secure said upper arm at a desired angle with reference to the longitudinal axis of said torso.

19. The apparatus of claim 15 further comprising an upper arm cuff having a retention tab, said upper arm cuff configured to encircle said upper arm proximate said elbow such that said retention tab is secured relative to said forearm retention member so as to discourage movement of said forearm retention member in a direction substantially parallel to said longitudinal axis of said forearm.

20. The apparatus of claim 19, wherein said retention tab is secured to said forearm retention member using a hook and loop fastener.

21. A method for manipulating an arm and shoulder extending from a torso of a patient positioned on a support surface, said arm of said patient including an upper arm extending from said shoulder to an elbow, and a forearm extending from said elbow to a hand, said method comprising the steps of:

A) positioning said patient relative to said support surface;

B) positioning an inflatable upper arm bladder between said torso and said upper arm of said patient and attaching said bladder relative to said patient such that said bladder is in contact approximate a proximal first portion of said upper arm;

C) securing a distal second portion of said upper arm relative to said torso of said patient such that said upper arm is discouraged from abduction relative to said torso of said patient, said distal second portion being located distal relative to said proximal first portion; and D) inflating said upper arm bladder so as to provide opposing first and second forces, said first force being against said upper arm of said patient and said second force being against said torso of said patient, said opposing forces being applied while said upper arm is discouraged from abduction relative to said torso of said patient pursuant to said securing step "C" such that a third force is applied proximate said distal second portion of said upper arm, said first and third forces combining to create a torque on said upper arm so as to elevate the humerus of said patient away from the glenoid of said patient due at least in part to said torque.

22. The method as claimed in claim 21, wherein said step "A" of attaching said bladder relative to said patient includes the use of at least one strap to strap said bladder relative to said patient.

23. The method as claimed in claim 22, wherein said step "A" of positioning said inflatable upper arm bladder between said torso and upper arm of said patient includes positioning said bladder in an armpit of said patient.

24. The method as claimed in claim 21, wherein said step "A" of attaching said bladder relative to said patient includes the use of at least one strap to strap said bladder relative to said supporting surface.

25. The method as claimed in claim 24, wherein said step "A" of positioning said inflatable upper arm bladder between said torso and upper arm of said patient includes positioning said bladder in an armpit of said patient.

26. The method as claimed in claim 21, wherein said step "A" of attaching said bladder relative to said patient includes the use of at least one strap to strap said bladder relative to said supporting surface and said patient.

27. The method as claimed in claim 26, wherein said step "A" of positioning said inflatable upper arm bladder between said torso and upper arm of said patient includes positioning said bladder in an armpit of said patient.

28. The method as claimed in claim 21, wherein said step "C" of securing said upper arm relative to said torso such that said upper arm is discouraged from abduction includes the use of a tension cuff and cable apparatus.

29. The method as claimed in claim 28, wherein said step "B" of positioning said inflatable upper arm bladder between said torso and upper arm of said patient includes positioning said bladder in an armpit of said patient.

30. The method as claimed in claim 21, wherein said step "B" of positioning said inflatable upper arm bladder between said torso and upper arm of said patient includes positioning said bladder in an armpit of said patient.

31. The method as claimed in claim 21, wherein step "C" is preformed by securing said forearm of said patient relative to said torso of said patient, such that said securement of said forearm tends to correspondingly secure the distal end of said upper arm, and said distal second portion of said upper arm being secured relative to said upper arm is said distal end of said upper arm due to its connection relative to said forearm at said elbow.

32. A method for manipulating an arm and shoulder extending from a torso of a patient positioned on a support surface, said arm of said patient including an upper arm extending from said shoulder to an elbow, and a forearm extending from said elbow to a hand, said method comprising the steps of:

positioning said arm of said patient such that the longitudinal axis of said forearm is substantially at a right angle relative to the longitudinal axis of said upper arm;

positioning an inflatable upper arm bladder adjacent said upper arm of said patient:

securing said upper arm bladder in place relative to a substantially stationary frame;

attaching said forearm relative to said substantially stationary frame by use of a sleeve configured to pass around and at least partially contain said forearm such that said forearm can rotate about an axis substantially parallel to said longitudinal axis of said forearm but is restricted from moving laterally in at least one direction relative to said longitudinal axis of said forearm; and inflating said upper arm bladder so as to provide a force against said upper arm of said patient so as to cause said upper arm and said forearm to rotate substantially about said axis substantially parallel to said longitudinal axis of said forearm such that the humerus of said patient is urged away from the glenoid of said patient.

33. A method for manipulating an arm and shoulder extending from a torso of a patient positioned on a support surface, said arm of said patient including an upper arm extending from said shoulder to an elbow, and a forearm extending from said elbow to a hand, said method comprising the steps of:

positioning said patient relative to said support surface;

positioning an inflatable upper arm bladder between said torso and upper arm of said patient and attaching said bladder relative to said patient;

securing said upper arm such that said upper arm is discouraged from abduction relative to said torso of said patient by use of a use of a tension cuff and cable apparatus, said apparatus including a cuff which is attached relative to the forearm of said patient; and inflating said upper arm bladder so as to provide an opposing first and second forces, said first force being against said upper arm of said patient and said second force being against said torso of said patient, said opposing forces being applied while said upper arm is discouraged from abduction relative to said torso of said patient, such that the humerus of said patient is urged away from the glenoid of said patient.

34. The method as claimed in claim 33, wherein said step of positioning said inflatable upper arm bladder between said torso and upper arm of said patient includes positioning said bladder in an armpit of said patient.

* * * * *